US012575939B2

(12) United States Patent
Freedman et al.

(10) Patent No.: US 12,575,939 B2
(45) Date of Patent: Mar. 17, 2026

(54) SPINAL FIXATION SYSTEM AND KIT

(71) Applicant: Mayo Foundation for Medical Education and Research, Rochester, MN (US)

(72) Inventors: Brett Freedman, Rochester, MN (US); Kendall Dennis, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 996 days.

(21) Appl. No.: 17/761,071

(22) PCT Filed: Sep. 15, 2020

(86) PCT No.: PCT/US2020/050820
§ 371 (c)(1),
(2) Date: Mar. 16, 2022

(87) PCT Pub. No.: WO2021/055323
PCT Pub. Date: Mar. 25, 2021

(65) Prior Publication Data
US 2022/0339002 A1     Oct. 27, 2022

Related U.S. Application Data

(60) Provisional application No. 62/901,157, filed on Sep. 16, 2019.

(51) Int. Cl.
*A61F 2/44*          (2006.01)
*A61F 2/46*          (2006.01)
(Continued)

(52) U.S. Cl.
CPC ............ *A61F 2/4455* (2013.01); *A61F 2/442* (2013.01); *A61F 2/4601* (2013.01);
(Continued)

(58) Field of Classification Search
CPC ........ A61F 2/442; A61F 2/4455; A61F 2/447; A61F 2/4601; A61F 2/4611; A61F 2002/30266; A61F 2002/30471; A61F 2002/30624; A61F 2002/30476; A61F 2002/30482; A61F 2002/30507;
(Continued)

(56) References Cited

U.S. PATENT DOCUMENTS 6,190,414 B1 *   2/2001   Young ..................... A61F 2/447
606/279
2010/0286777 A1   11/2010   Errico et al.
(Continued)

*Primary Examiner* — Samuel S Hanna
(74) *Attorney, Agent, or Firm* — Quarles & Brady LLP

(57)          ABSTRACT

A spinal fixation system includes an expandable disc replacement body and an angle-setting disc replacement holder; The expandable disc replacement body includes a first wall, a second wall, and a hinge connecting the first wall and the second wall. An insertion instrument may be used to implant the expandable disc replacement body into a subject. The disc replacement holder is positioned between the first wall and the second wall, and an angle and/or height between the first wall and the second wall can be varied by adjustment of the disc replacement holder and locked into place using locking mechanisms.

16 Claims, 19 Drawing Sheets

(51) Int. Cl.
    *A61F 2/28*            (2006.01)
    *A61F 2/30*            (2006.01)

(52) U.S. Cl.
    CPC ..... *A61F 2/4611* (2013.01); *A61F 2002/2835* (2013.01); *A61F 2002/30471* (2013.01); *A61F 2002/30507* (2013.01); *A61F 2002/3054* (2013.01); *A61F 2002/30579* (2013.01); *A61F 2002/30774* (2013.01); *A61F 2002/4615* (2013.01)

(58) Field of Classification Search
    CPC .. A61F 2002/30522; A61F 2002/30528; A61F 2002/30538; A61F 2002/30537
    See application file for complete search history.

(56)                   References Cited

U.S. PATENT DOCUMENTS

| | | | |
|---|---|---|---|
| 2011/0153020 A1 | 6/2011 | Abdelgany et al. | |
| 2011/0178599 A1* | 7/2011 | Brett ....................... | A61F 2/442 |
| | | | 623/17.16 |
| 2014/0114420 A1 | 4/2014 | Robinson et al. | |
| 2017/0246006 A1* | 8/2017 | Carnes .................. | A61F 2/4611 |
| 2018/0104066 A1* | 4/2018 | Bae ....................... | A61F 2/4611 |
| 2018/0303632 A1 | 10/2018 | Carnes et al. | |
| 2019/0183659 A1 | 6/2019 | Carnes et al. | |
| 2019/0231551 A1 | 8/2019 | Freedman et al. | |
| 2019/0247200 A1* | 8/2019 | Ulrich, Jr. ............. | A61F 2/4455 |
| 2019/0254838 A1* | 8/2019 | Miller .................... | A61F 2/447 |

\* cited by examiner

SPINAL FIXATION SYSTEM AND KIT

CROSS-REFERENCE TO RELATED APPLICATIONS

This application represents the national stage entry of PCT/US2020/050820 filed on Sep. 15, 2020 and claims priority to U.S. Patent Application No. 62/901,157 filed Sep. 16, 2019, the contents of which are incorporated herein by reference as if set forth in its entirety for all purposes.

STATEMENT REGARDING FEDERALLY SPONSORED RESEARCH

Not Applicable.

BACKGROUND

1. Field of the Invention

The invention relates to a fixation system for orthopedic or neurological surgery on a patient, and more particularly to a fixation system for anterior or lateral spine surgery, in which the primary intention is to fuse the spine.

2. Description of the Related Art

As an example, the most common method for surgically decompressing spinal cord or spinal nerve root compression at the level of the cervical spine is a procedure known as an anterior cervical discectomy and fusion. This procedure has been used successfully with minimal change in technique for several decades. Similar anterior and direct lateral approaches to the spine can be used to treat spinal disease at the thoracic, lumbar and lumbo-sacral levels as well. The current standard is that a piece of bone, bone substitute and/or a biomechanical interbody device, typically called a cage, is placed into the disc space following discectomy, and a plate may then be placed over the top of the disc space connecting the bone above and below the disc space via bone screws inserted through openings in the plate. The end goal is to have these two bones grow into one, which is called a fusion. This biological process is significantly enhanced by the rigidity added by the plate fixation and the biological substrate added by the bone or cage (which is filled with bone growth enhancing materials).

Recently, the functions of a plate and a cage have combined in devices that may be called screw-cages. However, these screw-cages provide suboptimal rigidity (especially in weakened bone) and the screws take up space or cause the bone graft chamber to be reduced in volume to accept the screw. This in turn can reduce the chances of achieving a biological fusion. Furthermore, these devices are largely mono-block in nature, which limits or eliminates their ability to conform to or actively change the shape of the space in which they are placed. Further, these devices are impacted into their final position. As such, the cages and more importantly the bone or bone graft substitute are not directly loaded into compression. It is well known to those versed in the art that bone heals best in compression, according to Wolff's Law. Further, when gaps between the graft and the vertebral endplates that are >1-2 mm are present, bone bridging is less common. Thus, an ideal device would be one that can encourage compression on the graft or at least minimize gapping between the graft and the vertebral endplates. Current devices do not possess the ability to directly compress the bone graft between the endplates of the vertebrae being fused. Furthermore, current devices provide no or limited access to the central grafting space once the device is implanted. This restricts or reduces the ability to place grafting material that can appose the upper and lower bones of the intended fusion segment. This is especially true, concerning cages that have properties of in-situ conformational change.

Increasing the lordosis of a disc space is generally a preferred goal of anterior and lateral spine fusion surgery. Life is a kyphosing event. Kyphosis shifts the center of gravity forward which causes the posterior paraspinal muscle to work harder to keep the body upright and increases the load on the anterior spine. The ability to dial in a preferred degree of lordosis is a significant advantage over conventional devices, such as the commonly used mono-block devices. Mono-block devices require the vertebral bodies to conform to the preferred angle as the device is impacted into its final position. However, spines of elderly patients, which is the largest growing population of spine surgery patients, tend to be stiffer and the bone is less dense, both of which reduce the likelihood of the mono-block device inducing the preferred lordotic angle. Conventional devices that may allow for in-situ lordosis correction utilize internally contained lordosis adjustment mechanisms. These mechanisms, which are most commonly driven by turning a screw, occupy space in the device. Most commonly, the central area of the device is occupied since placing the mechanism at the periphery would require dual mechanisms that simultaneously engage to produce an even lordosis effect. Occupying the central space with a mechanism precludes being able to place graft in this space, and thereby limits where biological fusion would have most commonly occurred. Biological fusion is the event that permanently reduces stress on the implant, finalizes the lordotic angle of the segment, and prevents late screw backout or other forms of implant failure. In fact, these devices are designed, intended, and marketed to encourage spinal fusion, thus, any improvement over the current art which enhances the ability for fusion to be obtained, while also affording the surgeon specific control over lordotic and disc height correction would markedly increase the efficacy of these procedures.

Other systems, which are not mono-block in nature, usually include complex adjustment mechanisms that are either prone to failure, difficult to use in a surgical setting, do not maintain their adjusted position, occupy a substantial portion of the space in which graft is typically placed in a mono-block cage or otherwise prevent bone in-growth and fusion based upon their complex designs. What is needed, therefore, is a spinal fixation system that would address these shortcomings.

SUMMARY OF THE DISCLOSURE

The present disclosure addresses the aforementioned drawbacks by providing fixation systems including adjustment and implantation devices, multi-level spinal fixation systems, and kits for spinal surgery. The disclosure also provides methods for fixing adjacent vertebrae in a spine that address the aforementioned drawbacks.

In one configuration, a method is provided for fixing adjacent vertebrae in a spine. The method includes inserting an expandable disc replacement body between vertebrae of the spine of a subject. The expandable disc replacement body includes a first wall, a second wall, a hinge connecting the first wall and the second wall, a first bone-screw receiving section at a proximal end of the first wall, and a second bone-screw receiving section at the proximal end of the second wall. The method also includes coupling an angle adjustment instrument to the expandable disc replacement body and adjusting an angle between the first wall and the second wall by movement of the angle adjustment instrument. The angle may be locked in place using a locking mechanism including a first arm coupled to the first wall, a second arm coupled to the second wall, and a first locking wall, wherein the first arm, second arm, and first locking wall are positioned between the first wall and the second wall.

In one aspect, the disclosure provides a spinal fixation system comprising an expandable disc replacement body and a locking mechanism. The expandable disc replacement body can include a first wall, a second wall, a hinge connecting the first wall and the second wall, a first bone-screw receiving section at a proximal end of the first wall, and a second bone-screw receiving section at the proximal end of the second wall. The locking mechanism can include a first arm coupled to the first wall, a second arm coupled to the second wall, and a first locking wall, wherein the first arm, second arm, and first locking wall are positioned between the first wall and the second wall. An angle between the first wall and the second wall can be locked in place at a time of implantation in a subject.

The spinal fixation system can include an angle adjustment instrument including a lever arm and a fulcrum for expanding the expandable disc replacement body. The angle adjustment instrument can be used to select the angle. The angle can be continuously varied between a lower value of the angle and an upper value of the angle by movement of the angle adjustment instrument. The angle adjustment instrument can include a bone graft introducer to push bone graft into a space in the expandable disc replacement body. The angle adjustment instrument can be configured to adjust the angle to a higher angle as bone graft is pushed into the space in the expandable disc replacement body, and the angle adjustment instrument can reduce the angle to a lower angle after the bone graft introducer is removed.

The angle adjustment instrument can include an instrument locking mechanism to hold the angle in place during implantation in the subject. The angle adjustment instrument can include a ratcheting mechanism to provide tactile feedback to a user regarding an amount of expansion of the expandable disc replacement body. The ratcheting mechanism can provide for 1 degree increments for the amount of expansion of the expandable disc replacement body. The angle adjustment instrument can include an angle guide to provide feedback to a user on the angle between the first wall and the second wall. The angle adjustment instrument can be an insertion instrument used to insert the spinal fixation system in the subject.

The spinal fixation system can further comprise an insertion instrument configured to insert the expandable disc replacement body into a spine of the subject.

In the spinal fixation system, the locking mechanism can include flexing the second arm to engage the first arm between the second arm and the first locking wall. The locking mechanism can include surface features on at least one of the first arm, second arm, first locking wall, or a combination thereof that interlock to lock the angle in place. The locking mechanism can include an aperture on the first arm that is larger than an aperture on the second arm, wherein the apertures are configured to receive a locking screw.

The hinge of the expandable disc replacement body can include a threaded portion for receiving the locking screw.

The spinal fixation system can further comprise a second locking mechanism including: a third arm coupled to the first wall, a fourth arm coupled to the second wall, and a second locking wall, wherein the third arm, fourth arm, and second locking wall are positioned between the first wall and the second wall. The second locking mechanism can include flexing the fourth arm to engage the third arm between the fourth arm and the second locking wall. The second locking mechanism can include surface features on at least one of the third arm, fourth arm, second locking wall, or a combination thereof that interlock to lock the angle in place.

The spinal fixation system can be created using a 3-D printer. The spinal fixation system can include a surface treatment, wherein the surface treatment includes at least one of a plasma coating, 3-D pores, a hydroxyapatite coating, metal abrasion, or metal pits.

In another aspect, the disclosure provides a method for fixing adjacent vertebrae in a spine. The method can include the steps of: (a) inserting an expandable disc replacement body between vertebrae of the spine of a subject, wherein the expandable disc replacement body includes a first wall, a second wall, a hinge connecting the first wall and the second wall, a first bone-screw receiving section at a proximal end of the first wall, and a second bone-screw receiving section at the proximal end of the second wall; (b) coupling an angle adjustment instrument to the expandable disc replacement body; (c) adjusting an angle between the first wall and the second wall by movement of the angle adjustment instrument; and (d) locking the angle in place using a locking mechanism including a first arm coupled to the first wall, a second arm coupled to the second wall, and a first locking wall, wherein the first arm, second arm, and first locking wall are positioned between the first wall and the second wall. In the method, step (c) can comprise expanding the expandable disc replacement body using a lever arm and a fulcrum of the angle adjustment instrument.

In the method, the angle can be continuously varied between a lower value of the angle and an upper value of the angle by movement of the angle adjustment instrument.

The method can further comprise introducing bone graft using a bone graft introducer coupled to the angle adjustment instrument to push bone graft into a space in the expandable disc replacement body.

The method can further comprise adjusting the angle to a higher angle using the angle adjustment instrument as bone graft is pushed into the space in the expandable disc replacement body, and reducing the angle to a lower angle after the bone graft introducer is removed using the angle adjustment instrument.

The method can further comprise holding the angle in place during implantation in the subject using an instrument locking mechanism coupled to the angle adjustment instrument.

The method can further comprise providing tactile feedback to a user regarding an amount of expansion of the expandable disc replacement body using a ratcheting mechanism coupled to the angle adjustment instrument.

In the method, the ratcheting mechanism can provide for 1 degree increments for the amount of expansion of the expandable disc replacement body.

The method can further comprise providing feedback to a user on the angle between the first wall and the second wall using an angle guide coupled to the angle adjustment instrument.

In the method, inserting the expandable disc replacement body into a spine of the subject can include using an insertion instrument.

In the method, the angle adjustment instrument can be the insertion instrument used to insert the spinal fixation system in the subject.

In the method, locking the angle in place using the locking mechanism can include flexing the second arm to engage the first arm between the second arm and the first locking wall.

The method can further comprise interlocking surface features on at least one of the first arm, second arm, first locking wall, or a combination thereof to lock the angle in place.

In the method, the locking mechanism can include an aperture on the first arm that is larger than an aperture on the second arm, wherein the apertures are configured to receive a locking screw.

In the method, the hinge of the expandable disc replacement body can include a threaded portion for receiving the locking screw.

The method can further comprise a second locking mechanism including: a third arm coupled to the first wall, a fourth arm coupled to the second wall, and a second locking wall, wherein the third arm, fourth arm, and second locking wall are positioned between the first wall and the second wall The method can comprise locking the angle in place using the locking mechanism includes flexing the fourth arm to engage the third arm between the fourth arm and the second locking wall.

The method can further comprise interlocking surface features on at least one of the third arm, fourth arm, second locking wall, or a combination thereof that interlock to lock the angle in place.

The method can further comprise creating the spinal fixation system using a 3-D printer. In the method, the spinal fixation system can include a surface treatment, and wherein the surface treatment includes at least one of a plasma coating, 3-D pores, a hydroxyapatite coating, metal abrasion, or metal pits.

In another aspect, the disclosure provides a spinal fixation system comprising: an expandable disc replacement body including a first wall, a second wall, a hinge connecting the first wall and the second wall; a locking mechanism including a first arm coupled to the first wall, a second arm coupled to the second wall, and a first locking wall, wherein the first arm, second arm, and first locking wall are positioned between the first wall and the second wall; an anterior plate configured to provide fixation for the expandable disc replacement body in a subject, wherein an angle between the first wall and the second wall is adjusted with an angle adjustment instrument, and the angle can be locked in place at a time of implantation in the subject.

In another aspect, the disclosure provides a kit for a spinal fixation system comprising: (i) an expandable disc replacement body including a first wall, a second wall, a hinge connecting the first wall and the second wall, and a locking mechanism including a first arm coupled to the first wall, a second arm coupled to the second wall, and a first locking wall, wherein the first arm, second arm, and first locking wall are positioned between the first wall and the second wall, (ii) an anterior plate configured to provide fixation for the expandable disc replacement body in a subject; and (iii) an angle adjustment instrument, wherein an angle between the first wall and the second wall is adjusted with the angle adjustment instrument, and the angle can be locked in place at a time of implantation in the subject. The kit can further comprise an insertion instrument configured to insert the expandable disc replacement body into a spine of the subject. In the kit, at least one of the insertion instrument and the adjustment instrument can be manufactured and sterile packed for single use.

In another aspect, the disclosure provides a spinal fixation system comprising: an expandable disc replacement body including a first wall, a second wall, a hinge connecting the first wall and the second wall, a first bone-screw receiving section at a proximal end of the first wall, and a second bone-screw receiving section at the proximal end of the second wall; a separate angle adjustment instrument capable of removably coupling to the expandable disc replacement body and creating a selected amount of angulation between the first wall and the second wall; a locking mechanism including a first arm coupled to the first wall, a second arm coupled to the second wall, and a first locking wall, wherein the first arm, second arm, and first locking wall are positioned between the first wall and the second wall and capable of rigidly maintaining the intended angulation between the first wall and the second wall, wherein an angle between the first wall and the second wall can be locked in place at a time of implantation in a subject.

In another aspect, the disclosure provides a kit for a spinal fixation system comprising: (i) an expandable disc replacement body including a first wall, a second wall, an anterior flange configured to provide fixation for the expandable disc replacement body in a subject, a hinge connecting the first wall and the second wall, and a locking mechanism including a first arm coupled to the first wall, a second arm coupled to the second wall, and a first locking wall, wherein the first arm, second arm, and first locking wall are positioned between the first wall and the second wall; and (iii) an angle adjustment instrument, wherein an angle between the first wall and the second wall is adjusted with the angle adjustment instrument, and the angle can be locked in place at a time of implantation in the subject. The kit can further comprise an insertion instrument configured to insert the expandable disc replacement body into a spine of the subject. In the kit, at least one of the insertion instrument and the adjustment instrument can be manufactured and sterile packed for single use.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

Like reference numerals will be used to refer to like parts from Figure to Figure in the following description of the drawings.

DETAILED DESCRIPTION

Figure 1A:
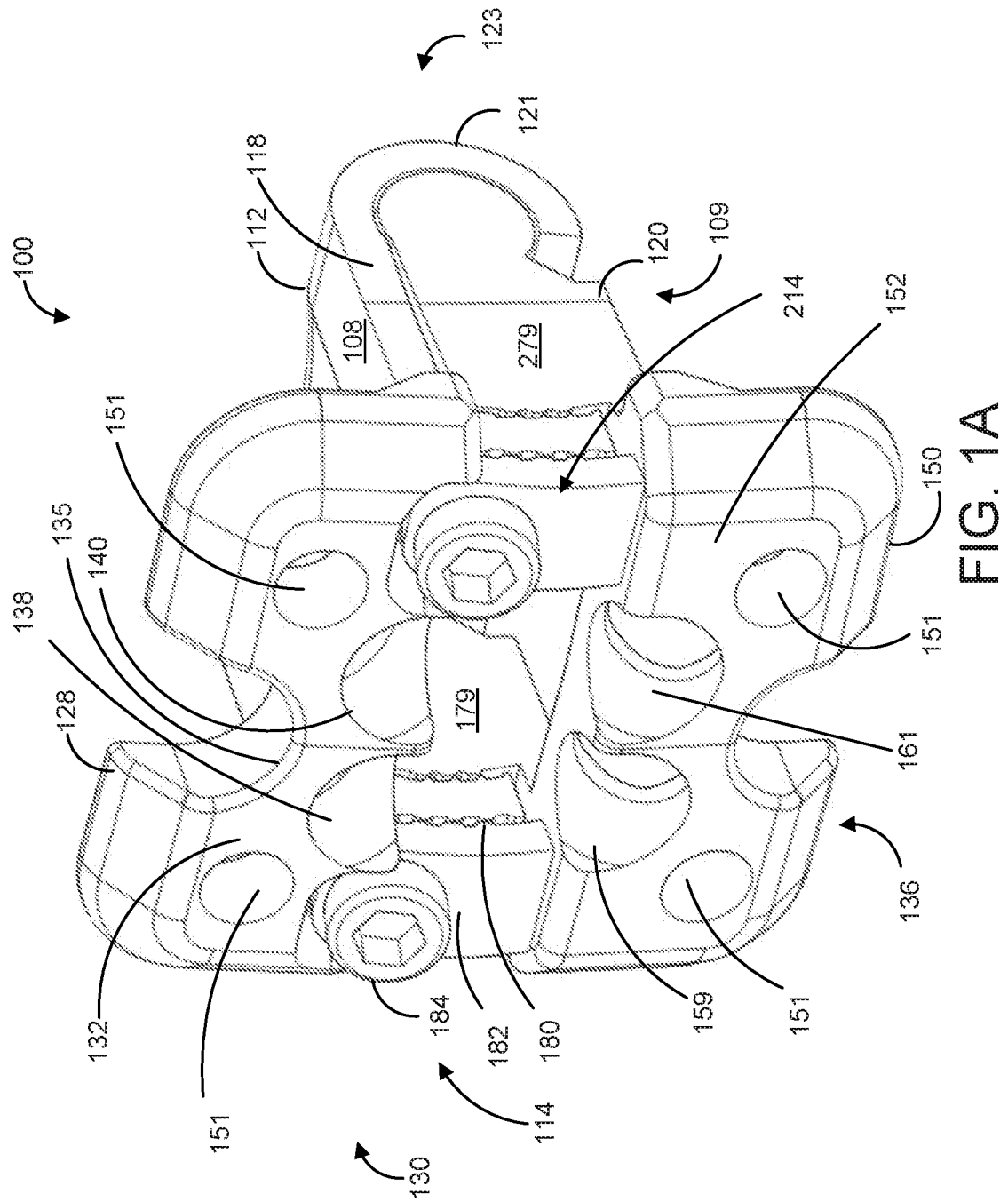
FIG. 1A is a front perspective view of one configuration for a spinal fixation system expandable disc replacement body.
Figure 1B:
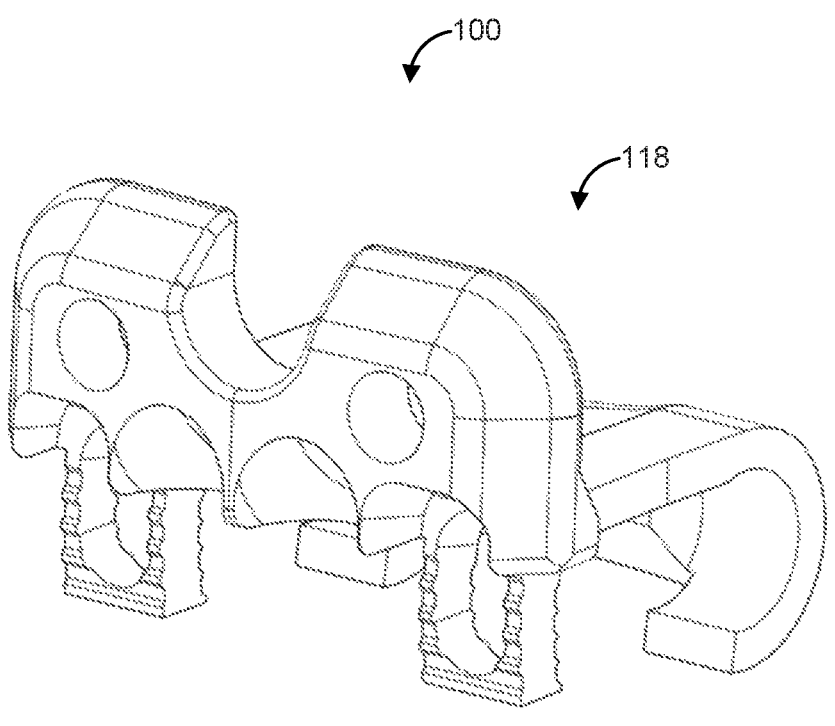
FIG. 1B is a front perspective view of a first wall of the expandable disc replacement body of FIG. 1A.
Figure 1C:
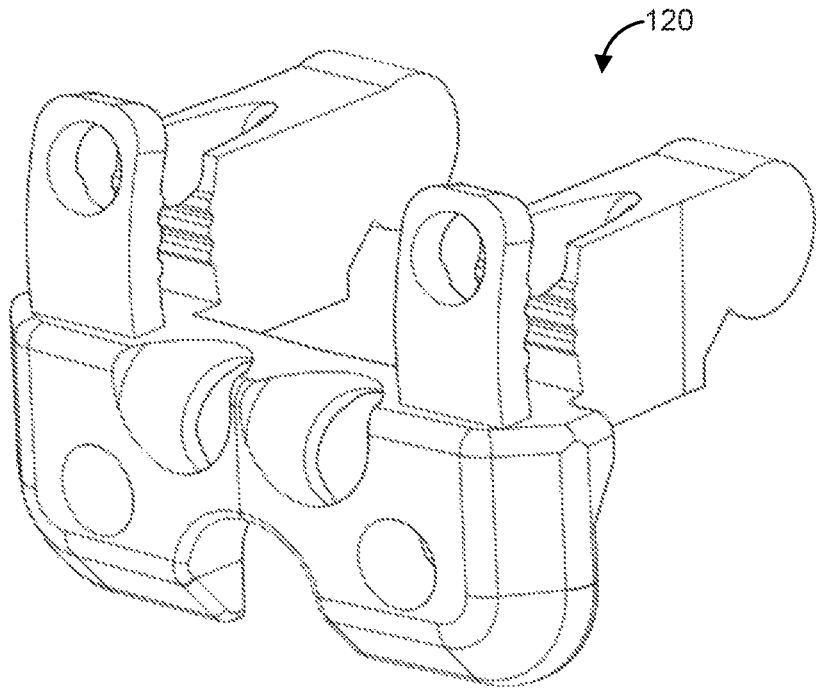
FIG. 1C is a front perspective view of a second wall of the expandable disc replacement body of FIG. 1A.

Referring to FIGS. 1A-5, there is shown an embodiment of a spinal fixation system 100 according to the present disclosure. Spinal fixation system 100 includes an expandable disc replacement body 112, and a first locking mechanism 114, and may also include a second locking mechanism 214, an insertion instrument and an angle-adjusting disc replacement holder instrument. Expandable disc replacement body 112 includes a first wall 118, a second wall 120, a hinge 121 attaching first wall 118 and second wall 120 at a distal end 123 of expandable disc replacement body 112, upper endplate 108, lower endplate 109, and two lateral sides 124. Pin holes 151 may provide for coupling to an angle adjuster instrument that opens expandable disc replacement body 112 as discussed below. First locking mechanism 114 may allow for an angle to be locked in place and includes first arm 180 coupled to first wall 118, second arm 182 coupled to second wall 120, and first locking wall 179. First arm 180 is locked in place by being held between second arm 182 and first locking wall 179 using locking screw 184. First arm 180, second arm 182, and first locking wall 179 may include surface features 201 that interlock and prevent spinal fixation system 100 from moving after being locked in place. Disc replacement body 112 may comprise a metallic material, such as titanium, cobalt chrome or stainless steel, a polymeric material, such as polyetheretherketone, or a ceramic material. The surfaces of the disc replacement body that will lie in contact with the patient's bone when the device is implanted may have surface coatings, like hydroxyapatite or plasma sprayed metal particles, or surface preparations, like acid etching, applied at fabrication or prior to insertion, that encourage bone integration with the surface of the disc replacement body. One or a plurality of disc replacement body 112 devices may be implanted into a subject.

First wall 118 of expandable disc replacement body 112 includes a first space 126 for receiving bone graft, such as allograft bone, and a first bone-screw receiving section 128 located on a proximal end 130 of first wall 118. First bone-screw receiving section 128 includes a first flange 132, and a first grasping recess 135 on an inferior edge 136 of first bone-screw receiving section 128. First bone-screw receiving section 128 may be angled back from vertical to decrease the profile. First bone-screw receiving section 128 and second bone-screw receiving section 150 may include an all-around chamfer added to the top, bottom, and sides to create a smooth transition from bone to implant to minimize trauma to soft tissue. First flange 132 may terminate in an overhang to prevent bone graft from backing out of first space 126. First flange 132 includes a first opening 138 and a second opening 140. First opening 138 defines a first longitudinal axis 141, and is configured to receive a first bone screw. Second opening 140 similarly defines a second longitudinal axis 145, and is configured to receive a second bone screw. First longitudinal axis 141 and second longitudinal axis 145 diverge in a direction toward the distal end 123 of expandable disc replacement body 112. Snap rings, and the like, can be used in first opening 138 and second opening 140 to effectively block the first and second bone screws from backing out. First flange 132 may include additional holes at medial and lateral end sections of first flange 132 so that sutures can be threaded through the holes and tied to hold expandable disc replacement body 112 in place. The anterior graft window or first space 126, may allow for grafting material to be placed after the device is fully implanted and in its final conformation. This allows for grafting material to be more ideally placed in direct apposition with the vertebral bone of the adjacent levels being fused.

Second wall 120 of expandable disc replacement body 112 may include a second space 149 for receiving bone graft, and a second bone-screw receiving section 150 located on a proximal end 130 of second wall 120. Second bone-screw receiving section 150 may be angled back from vertical to decrease the profile, as described above. Second bone-screw receiving section 150 includes a second flange 152. Second flange 152 may terminate in an overhang to prevent bone graft from backing out of second space 149. Second flange 152 includes a third opening 159 and a fourth opening 161. Third opening 159 defines a third longitudinal axis 162, and is configured to receive a third bone screw. Fourth opening 161 defines a fourth longitudinal axis 170, and is configured to receive a fourth bone screw. Third longitudinal axis 162 and the fourth longitudinal axis 170 also diverge in a direction toward distal end 123 of expandable disc replacement body 112. In some configurations, snap rings can be used in third opening 159 and fourth opening 161 to effectively block the third and fourth bone screws from backing out. Second flange 152 may include additional holes at medial and lateral end sections of second flange 152 so that sutures can be threaded through the holes and tied to hold expandable disc replacement body 112 in place.

Hinge 121 of expandable disc replacement body 112 may be formed using a first arcuate structure 101 at the distal end of first wall 118, an opposed second arcuate structure 102 at the distal end of first wall 118, a first cylindrical structure 191 at the distal end of second wall 120, and a second cylindrical structure 192 at the distal end of second wall 120. In some embodiments, not illustrated herein, both lordotic angle correction and vertical translation may be provided either separately or in concert, where hinge 121 can be cam-shaped or have an otherwise non-arcuate shape that enables adjustment in more than one plane. As depicted in FIGS. 1A-5, first arcuate structure 101 surrounds first cylindrical structure 191 for rotation of first arcuate structure 101 with respect to the first cylindrical structure 191, and second arcuate structure 102 surrounds second cylindrical structure 192 for rotation of second arcuate structure 102 with respect to the second cylindrical structure 192. Hinge 121 may include a bar 125 connecting first arcuate structure 101 and second arcuate structure 102. Bar 125 may be convex on a side facing first space 126 of first wall 118.

Hinge 121 or posterior ends of first wall 118 and second wall 120 may include a rounded portion for distal end 123 to direct/pry the adjacent vertebral bodies apart as the device is inserted. This may allow for the implanted system to be taller than the native disc space, which may allow for indirect decompression of the neuroforamen and spinal canal.

A first arcuate length of first arcuate structure 101 may be used to limit the angular rotation of first arcuate structure 101 about first cylindrical structure 191 in that a terminal end 105 of first arcuate structure 101 contacts a stop wall 106 that extends from first cylindrical structure 191. The angular location of terminal end 105 of first arcuate structure 101 may be determined by varying the first arcuate length of first arcuate structure 101. Likewise, a second arcuate length of second arcuate structure 102 may be used to limit the angular rotation of second arcuate structure 102 about second cylindrical structure 192 in that a terminal end 115 of second arcuate structure 102 contacts a stop wall 116 that extends from second cylindrical structure 192. The angular location of terminal end 115 of second arcuate structure 102 may be determined by varying the second arcuate length of second arcuate structure 102. In one non-limiting embodiment, the angular rotation of first arcuate structure 101 about first cylindrical structure 191 and the angular rotation of second arcuate structure 102 about second cylindrical structure 192 can be varied between a lower value of the angle of 0° and an upper value of the angle of 30°. In a non-limiting example of a cervical spine application, an upper value of 12° may be used. In another non-limiting example of a lumbar spine application, an upper value of 30° may be used. The anatomic application, or the overall size of the device may determine the upper value of the angle.

In order to easily assemble spinal fixation system 100, slots can be arranged in the lateral sidewalls of first flange 132. First flange 132 can then slide onto second flange 152.

Referring again to FIG. 1A, the capability to change the angle between first and second walls 118, 120 allows for expandable disc replacement body 112 to be used to counteract various degrees of lordosis of the spine. First and second locking mechanisms 114, and 214 can include markings on first arm 180 and third arm 280 where the markings correlate with a change in the angle between first and second walls 118, 120. The difference between the first and second adjustment angles may create a slight lateral angle between first and second walls 118, 120, which may further be used to counteract scoliosis of the spine. In this case, hinge 121 may alternatively be formed of a pliable material coupling first and second walls 118, 120 to allow for biaxial rotation.

First locking mechanism 114 includes first arm 180 coupled to first wall 118 and second arm 182 coupled to second wall 120. First arm 180 is locked in place with second arm 182 and first locking wall 179 using locking screw 184. First arm 180 and second arm 182 may include surface features 201 that interlock and prevent spinal fixation system 100 from moving after being locked in place. Second arm 182 includes a second arm aperture 188 configured to allow the threads of locking screw 184 to pass through, but to prevent the head of locking screw 184 from passing through. First arm 180 includes an elongated first arm aperture 183 configured to allow locking screw 184 to pass through and threadably engage a first internally threaded cylinder 187, which is a portion of second cylindrical structure 192. In some configurations, a washer 197 may be used to prevent locking screw 184 from backing out.

In some configurations, locking an angle in place between first and second walls 118, 120 may include flexing or otherwise bending second arm 182 so as to pinch, squeeze, or sandwich first arm 180 between second arm 182 and the first locking wall 179. Flexing or bending second arm 182 may be provided by the force of the locking screw 184 pulling the second arm 182 towards first locking wall 179. Surface features 201 may be used on any or all of the surfaces of first arm 180, second arm 182, and first locking wall 179 to aid in locking the angle in place. The locking wall configurations may add rotational control, as the two horizontal surfaces glide between each other, when the device is not locked, and then prevent axial rotation when the device is locked, due to their affacement.

In some configurations, the surfaces between the arms on the first and second walls 118 and 120 respectively, have teeth or grooves that result in interdigitation. These teeth/grooves can be spaced to deliver a specified lordotic angular correction between each successive tooth/groove interdigitation. Further, this interdigitation may allow for a rigid locking mechanism to hold the final lordotic angular correction. In addition to compressing the arms against each other via a lordotic angle locking screw housed within the lateral walls of the device, the distal end of this lordotic angle locking screw can have a capture mechanism contained within the lateral wall, that prevents spontaneous or non-forceful/unintended back out of the lordotic angle locking screw. Thus, providing a double mechanism for locking the final confirmation of the device in-situ.

An angle adjustment instrument may be used to select the angle, and in some configurations the final resting height of the implant. This conformational change occurs after the implant is fully seated in the intervertebral space. This adjustment instrument may obviate the need for an intrinsic gearing mechanism in the implant, which thereby frees up space for a larger grafting cavity and/or a thicker more robust construction of the implant. The concept described herein is termed, "ex-situ" conformational correction. The angle adjustment instrument may also include an instrument locking mechanism to hold the angle in place during implantation in the subject, or more commonly to correct the angulation between vertebral bodies after the cage has been fully seated into the disc space.

In some configurations, a second locking mechanism 214 may be used with spinal fixation system 100. Second locking mechanism 214 includes a third arm 280 coupled to first wall 118, fourth arm 282 coupled to second wall 120, and second locking wall 279. Third arm 280 is locked in place by being held between fourth arm 282 and second locking wall 279 using locking screw 284. Third arm 280, fourth arm 282, and second locking wall 279 may include surface features 202 that interlock and prevent the spinal fixation system 100 from moving after being locked in place. Fourth arm 282 includes a second arm aperture 288 configured to allow the threads of locking screw 284 to pass through, but to prevent the head of locking screw 284 from passing through. Third arm 280 includes an elongated first arm aperture 283 configured to allow locking screw 284 to pass through and threadably engage a first internally threaded cylinder 287, which is a portion of first cylindrical structure 191. In some configurations, a washer 199 may be used to prevent locking screw 284 from backing out.

In some configurations, locking an angle in place between first and second walls 118, 120 may include using the second locking mechanism 214 by flexing or otherwise bending fourth arm 282 so as to pinch, squeeze, or sandwich third arm 280 between fourth arm 282 and the second locking wall 279. Flexing or bending fourth arm 282 may be provided by the force of the locking screw 284 pulling the fourth arm 282 towards second locking wall 279. Surface features 202 may be used on any or all of the surfaces of third arm 280, fourth arm 282, and first locking wall 279 to aid in locking the angle in place.

In another locking option, locking screws 184 and 284 may be locked in place using a tine, which may be mounted to body 112 and bent to block screws 184 and 284 from backing out. Once the final position of expandable disc replacement body 112 has been set, the tine could be bent into each screw head's slot. The slot could be modified to include more than one final vertical position required to receive the tine. For example, an "X" shape pattern, or a "+" shape pattern, or a "*" shape pattern could be incorporated on the screw head, allowing for more position options of the screw head's position. Using this principle, if the tine is bent into the screw head's slot, the screw cannot turn, and therefore will not back-out/protrude after its final position is set.

In some configurations, surface features 201, 202 may interlock at predetermined angles between first and second walls 118, 120. In this way, surface features 201, 202 may act similar to a ratcheting mechanism where each tooth or shape of surface features 201, 202 corresponds to 0.5 degree, or 1 degree, or other selected angle amount of expansion between first and second walls 118, 120. The surgeon is not confined to locking expandable disc replacement body 112 at angles of integer value, nor is the surgeon confined to locking expandable disc replacement body 112 at largely spaced intervals (i.e., 3.2, 3.4, 3.6, 3.8 degrees), as surface features 201, 202 may be configured with any angles at predetermined locations. Surface features 201, 202 may also be absent allowing for infinite degree settings for the angles on smooth surfaces.

Figure 5:
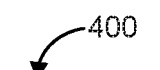
FIG. 5 is a front perspective view of one configuration for a spinal fixation system with an expandable disc replacement body with an anterior plate.

Referring to FIG. 5, an anterior plate 400 configured for use with the body 112 is shown. In some configurations, bone screws may not be used to provide fixation through first and second openings 138, 140, and the third and fourth openings 159, 161, respectively, as shown in FIG. 1A. Alternatively to the use of bone screws, fixation may be provided by use of an anterior plate 410. Anterior plate 410 may provide for an all-interbody configuration. Anterior plate 410 may include bone screw holes 420, where fixation of the plate is provided, and anterior plate 410 would then hold body 112 in place such as by placing pressure upon the face of body 112 rather than through the use of bone screws through body 112. Anterior plate 400 may provide stabilization for the body 112. The anterior flange of the expandable disc replacement body 112 may include ridges, slots and/or indentations or other surface features that serve as an anchor point for anterior plate 400 and prevent plate 400 from slipping from a selected position with body 112. To provide for coupling of the anterior plate 400 to the bone of the subject, plate 400 may have ridges, slots, and/or indentations or other surface features that serve as an anchor.

The ridges or slots and the like that provide connection between plate 400 and the bone of the subject, and between plate 400 and the body 112 may also allow for a single-handed operation by the surgeon during implantation. In a conventional procedure, a surgeon may need to dedicate a hand to holding an implant in place because it needs to be held still in a specific location against the anterior surface of the vertebrae, deep inside the body. However, the surgeon also may need to use both hands to create a pilot hole for the bone screw, such as using one hand to hold the drill guide so soft tissue is not caught by the spinning drill bit and the other hand to hold the drill. In some configurations to provide for a single-handed operation, anterior plate 400 may include male-female pattern areas for contact with the bone, which may semi-rigidly hold anterior plate 400 in the desired location. By semi-rigidly holding plate 400 in place, the 2-hands of the surgeon may be free to focus on the drill and drill guide and plate 400 may be prevented from slipping during the procedure.

The anterior flange of expandable disc replacement body 112 may have different configurations depending upon the desired application and may also protect against over insertion of the device, which can contuse or injury the spinal cord, in addition to providing for fixation. FIG. 1A depicts two bone-screw holes for first wall 118 and second wall 120. In another configuration, first wall 118 and second wall 120 may include one screw hole in each flange, which may be placed either centrally or paracentrally. For paracentral screw locations, the upper and lower screw holes may be off-set. In a non-limiting example, the upper screw hole could be right paracentral and the lower screw hole could be left paracentral. A configuration where one screw hole is placed paracentrally may be configured to work with an anterior plate 400.

Plate 400 may include docking sites on the upper anterior flange that cause plate 400 to "snap" into place or otherwise stay in the desired location, which may include an orientation with respect to the inserted expandable disc replacement body 112. Screw holes may be prepared through the plate and bone-screws may be inserted without concern for plate 400 migrating or taking on an undesirable relationship to the implanted expandable disc replacement body 112.

In some configurations, the bottom of anterior plate 400 would not semi-rigidly engage the bottom anterior flange of expandable disc replacement body 112, as this may require numerous specifically sized plates to fit different body heights and lordotic angulations. Anterior plate 400 may include a rectangular "0" shape, such as being open in the middle, with thickened side rails that fit left and right in recessed portions of the anterior aspect of expandable disc replacement body 112. A shape of this form may provide for three sides of tight conformity between anterior plate 400 (upper, left and right) and expandable disc replacement body 112, while allowing for the matched plate to have its lower bone-screw holes fit immediately below the lower anterior flange depending on the height and lordotic angle of the inserted expandable disc replacement body 112.

In some configurations, anterior plate 400 includes two screw holes 420 per vertebral level, as shown in FIG. 5. Alternatively, plate 400 may include only one screw hole 420 per level, such as for holding longer constructs that span multiple vertebrae. In some configurations, the ends of the construct may include two screw holes 420, but the central vertebrae, such as those that are not the top or bottom vertebrae, may include one screw hole 420. One screw hole 420 of anterior plate 400 could directly overlie the single hole in expandable disc replacement body 112, which allows for a single screw to secure the plate and expandable disc replacement body 112 to the vertebral bone. A remaining screw hole 420 in plate 400 may accept a screw that passed through plate 400 directly into the vertebral body without passing through expandable disc replacement body 112. To further assist implantation, a small set screw could be inserted through plate 400, into the expandable disc replacement body 112 that further holds plate 400 in place during insertion. This set screw could remain permanently or be removed once plate 400 and body 112 are fully inserted and screwed into place. In some configurations, anterior plate 400 may include central cut-outs that fit around the anterior prominences of expandable disc replacement body 112, such that when mated they do not add to the overall anterior projection of the implant from the anterior surface of the vertebral body.

Anterior plate 400 may be constructed of any suitable material, such as a material that matches body 112, a metal, titanium, and the like. The material may be selected to provide a rigid anterior linkage between the upper and lower vertebrae and may be conformed such that it mates to the anterior surface of body 112 to prevent excessive anterior projection of the plate.

In some configurations, anterior plate 400 may be coupled to the expandable disc replacement body 112 prior to implantation of the expandable disc replacement body 112 and plate 400 into the subject. A trial system may be used to determine what footprint, disc height, and lordotically angled device, may be needed for a subject. This trial system may include mono-block inserts that have a specific, fixed height, width, depth and angulation. Trials devices may also include an intrinsic mechanism (e.g. screw driven, and the like) that allows for in-situ changes in the height and/or lordotic angulation of the trial, to allow for identification of the proper expandable disc replacement to use. In some configurations of a trial device, there may also be an adjustment for depth. This would allow for the least number of trial inserts needed, to allow one to explore all potential combinations of implant height, depth, width and lordotic angulation available within the system. A specific expandable disc replacement body 112 may then be selected and it may be opened into the sterile surgical field. The selected expandable disc replacement body 112 could be angulated to the trialed degree of lordosis and an anterior stabilizing plate 400 that fits the body 112 in a desired manner may be selected. Assembly may be performed and tested on a "back table" in the operating room. Expandable disc replacement body 112 could then be closed back down to 0 degree angle for insertion into the subject. Quality assurance testing may also be satisfied by checking to make sure that the lordosis angulating portion of expandable disc replacement body 112 works prior to insertion. Anterior plate 400 may then be "sandwiched" between expandable disc replacement body 112 and an insertion instrument, such as discussed below.

In one configuration, expandable disc replacement body 112 does not include screw holes, and instead fixation is provided by anterior plate 400. An anterior flange may be used with body 112 to prevent over-insertion of the device, which can lead to spinal cord injury. As above, the disc space may be trialed, and then an expandable disc replacement body 112 may be selected. Expandable disc replacement body 112 may be opened to the preferred lordosis and a best fit anterior plate 400 may be selected. Test assembly and insertion may proceed as above and may include a set screw that temporarily or permanently connects anterior plate 400 to body 112. The vertebral facing portion of plate 400 may be thickened and grooved to strengthen plate 400, and so that it conforms and possible male-female engages to the upper end of the anterior flange of the upper side of the expandable disc replacement body 112. The upper two screw holes 420 may be used to secure plate 400 and expandable disc replacement body 112 to the spinal column. The lower screw holes 420 may not be used. An implantation instrument configured for use with anterior plate 400 may then be affixed to the anterior surface of expandable disc replacement body 112 and the lordosis that was trialed may be set. The anterior flange of the lower side of disc replacement body 112 may approximate or contact the upper portion of the lower aspect of anterior plate 400. This may indicate that body 112 has been fully opened to match the lordosis that was achieved at trialing and may result in a good fit of anterior plate 400 to the space immediately above and below expandable disc replacement device 112. One skilled in the art will appreciate that expandable disc replacement body may have a plurality of screw holes, a single screw hole, or may not have any screw holes when used with an anterior plate 400.

Figure 6A:
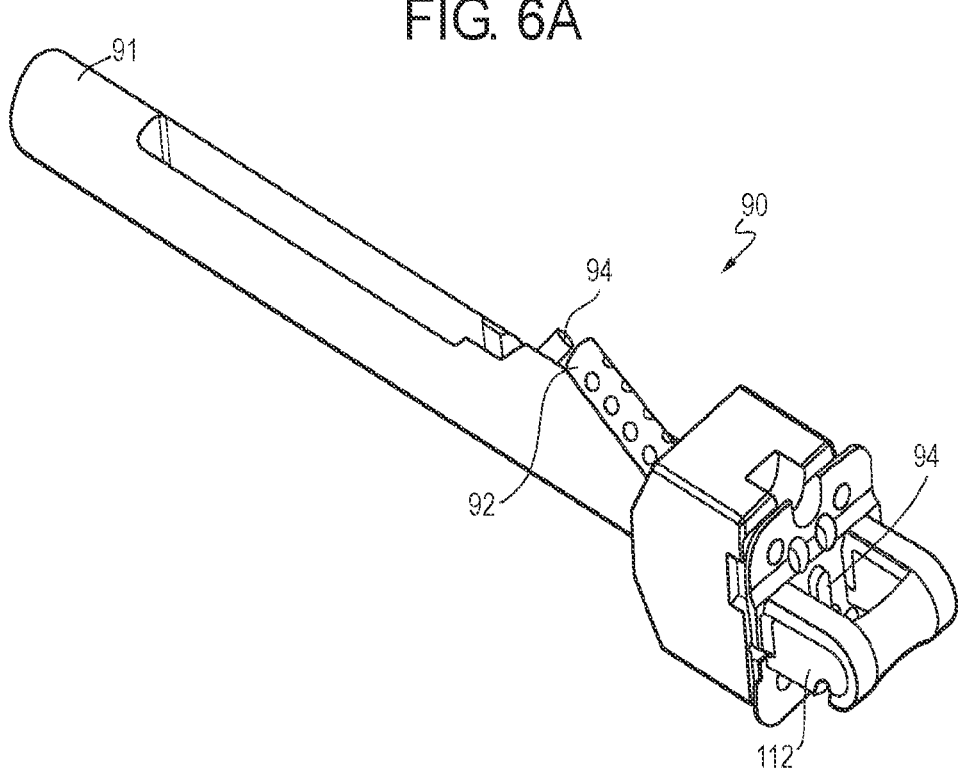
FIG. 6A is a front perspective view of a non-limiting example insertion instrument.
Figure 6B:
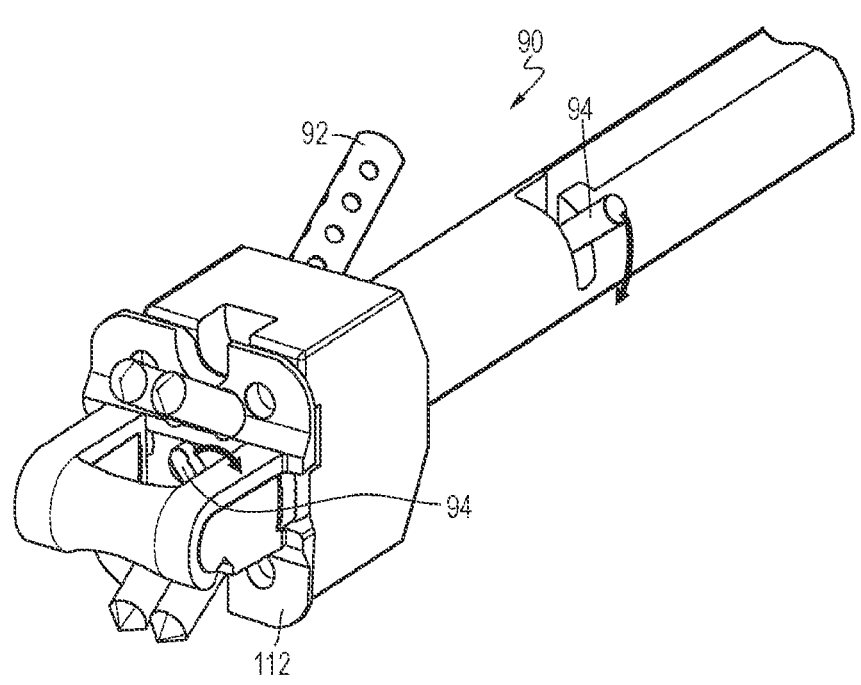
FIG. 6B is an expanded view of a front perspective view of the non-limiting example insertion instrument of FIG. 6A.
Figure 6C:
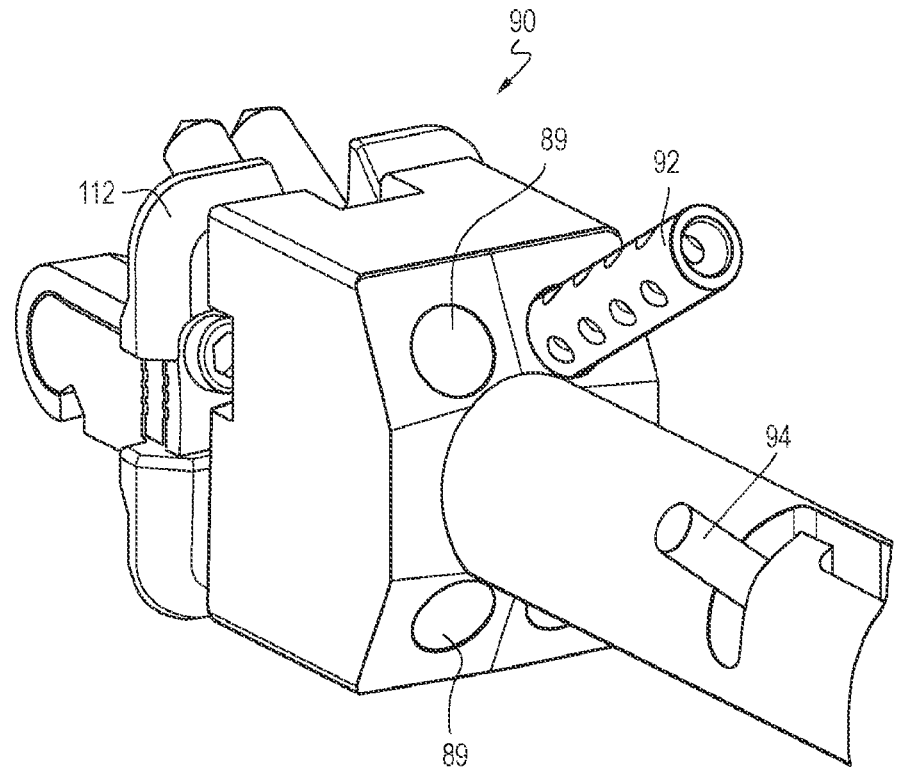
FIG. 6C is an expanded view of a rear perspective view of the non-limiting example insertion instrument of FIG. 6A.
Figure 7A:
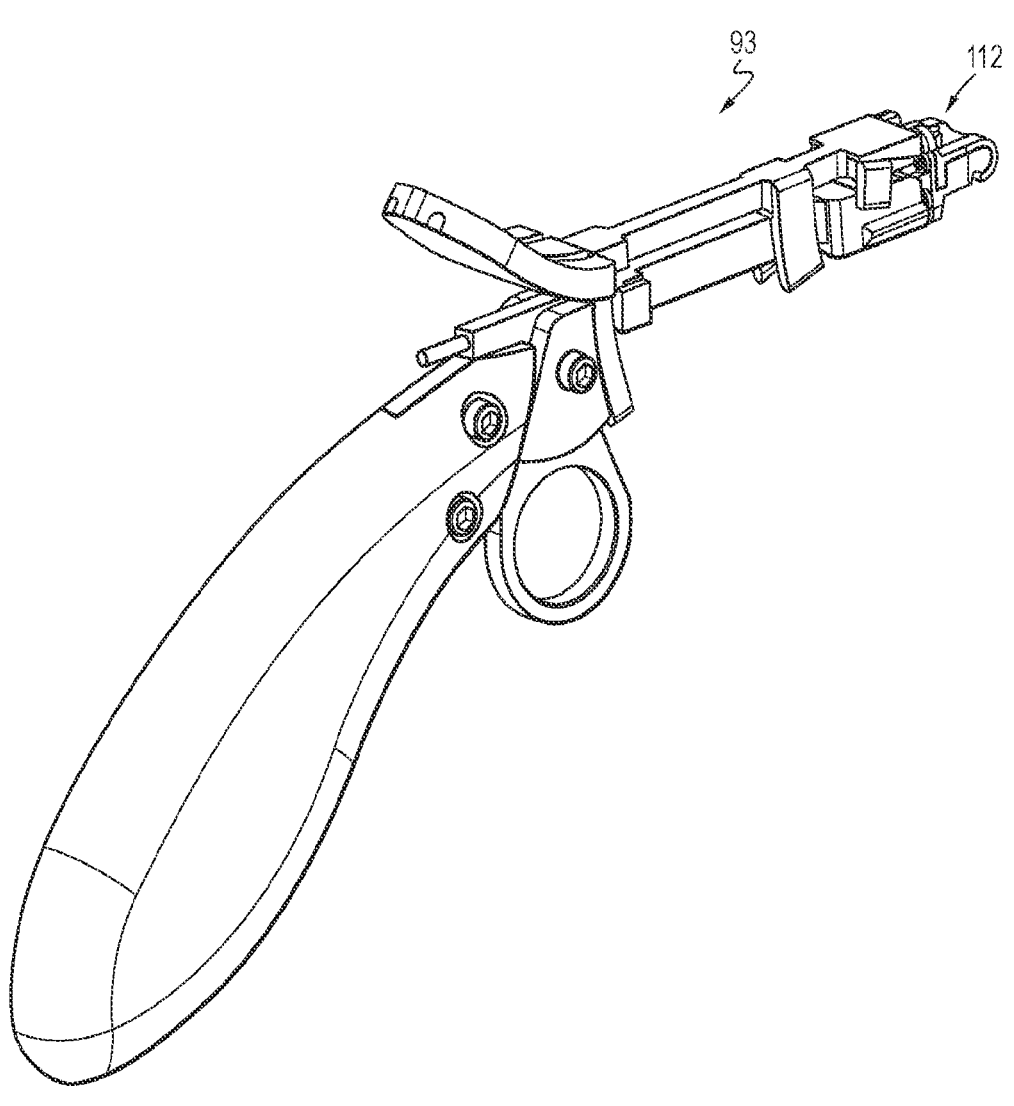
FIG. 7A is a rear perspective view of a non-limiting example disc replacement holder device.
Figure 7B:
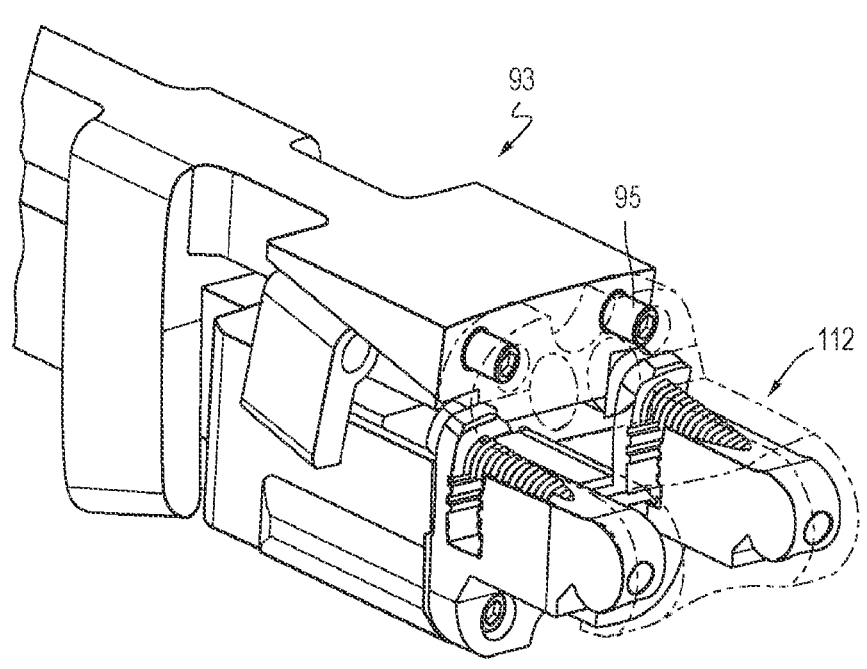
FIG. 7B is a zoomed-in front perspective view of the disc replacement holder of FIG. 7A holding the spinal fixation system of FIG. 1A.
Figure 8:
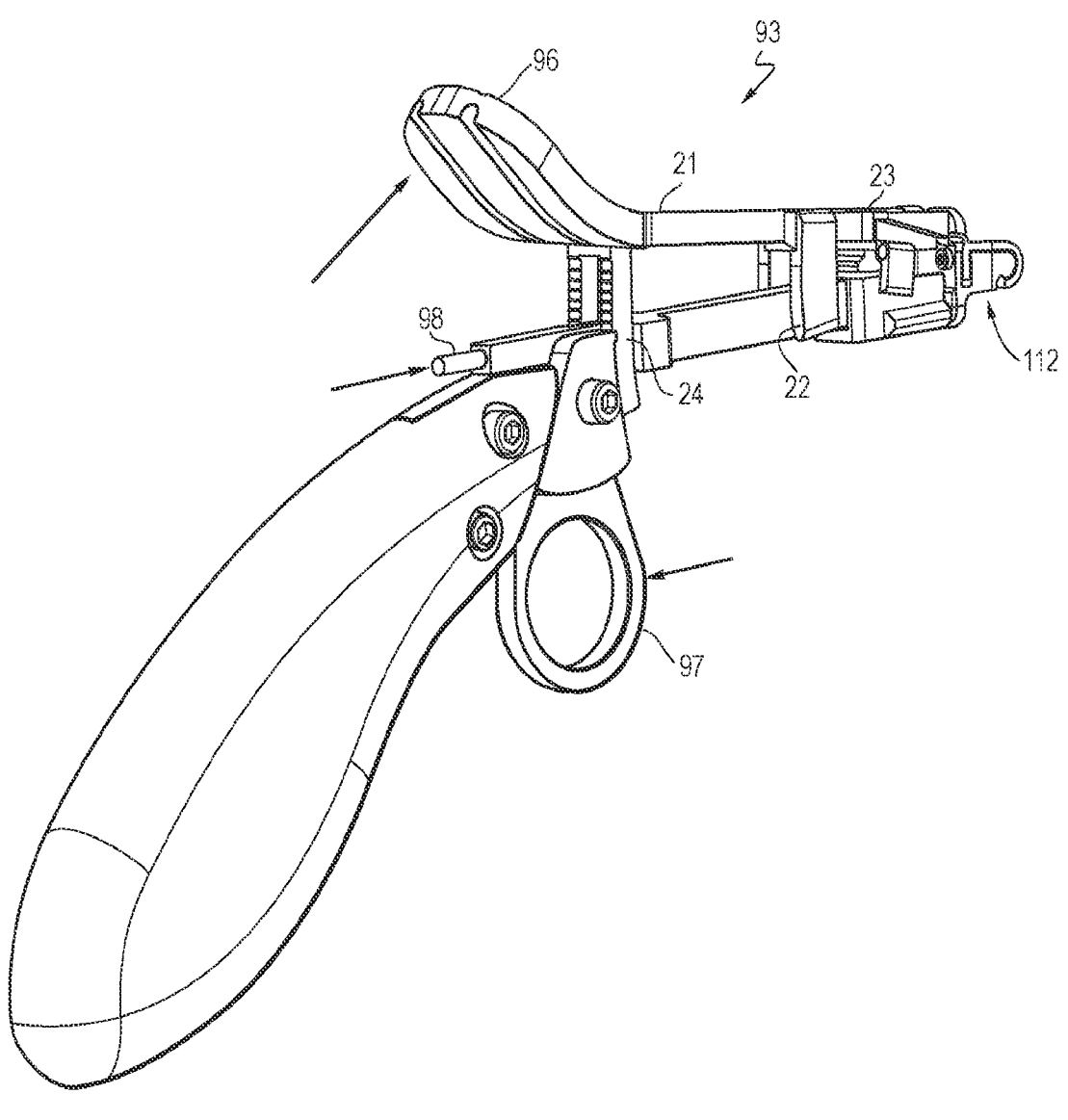
FIG. 8 is another rear perspective view of the disc replacement holder device of FIG. 7A.
Figure 9:
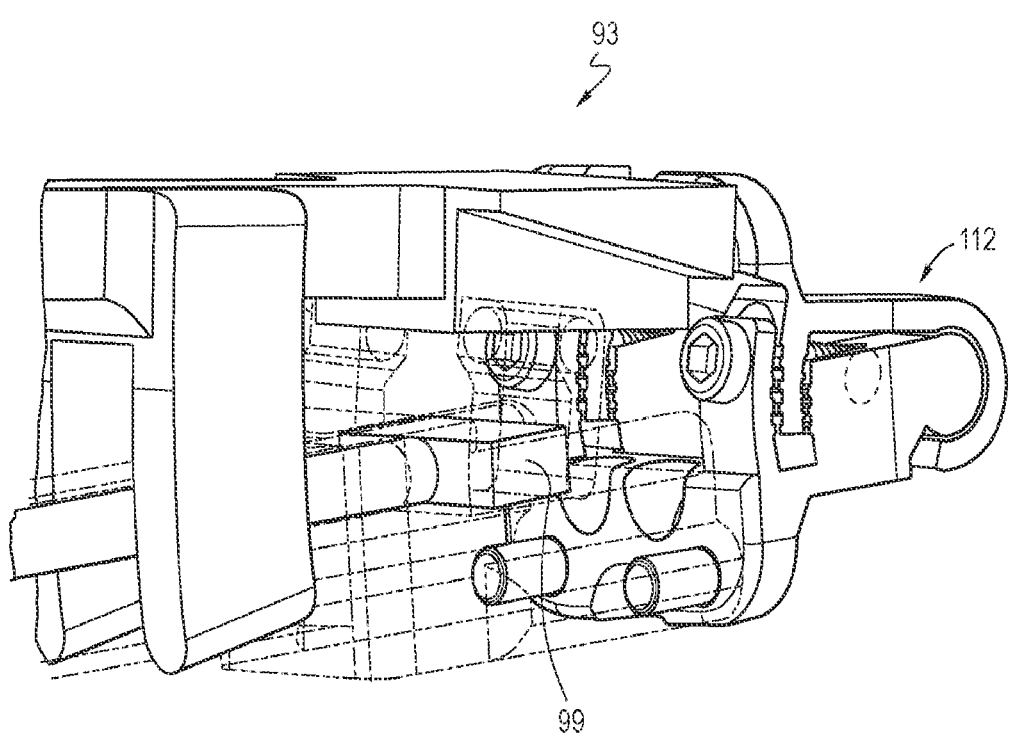
FIG. 9 is a zoomed-in rear perspective view of the disc replacement holder of FIG. 7A holding the expandable disc replacement body of FIG. 1A with a portion of the disc replacement holder made transparent.
Figure 10:
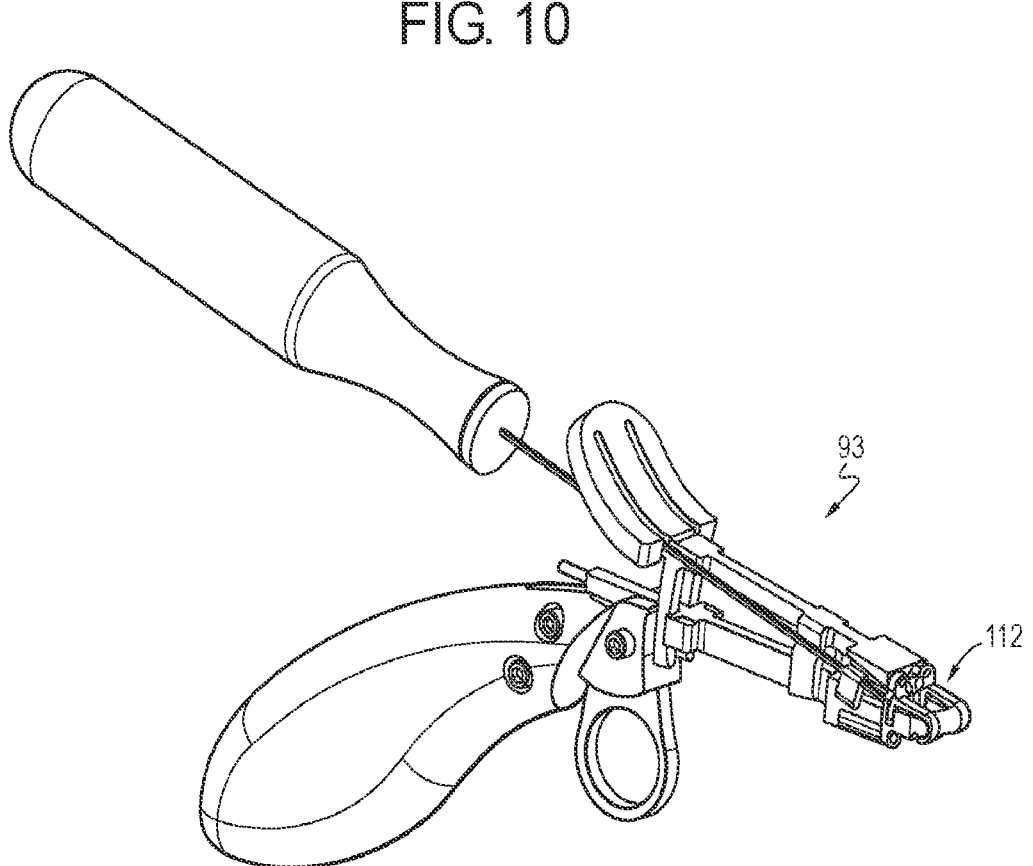
FIG. 10 is a front perspective view of the disc replacement holder of FIG. 7A holding the expandable disc replacement body of FIG. 1A.

Referring to FIGS. 6A-6C, a non-limiting example of an insertion instrument 90 is shown. Insertion instrument 90 includes insertion block 91, implant lock lever 94, and drill guide 92. The expandable disc replacement body implant 112 is placed at the distal end of insertion block 91. By pushing down on the implant lock lever 94, a user can secure the implant, such as expandable disc replacement body 112, on the distal end of insertion block 91. With expandable disc replacement body 112 secured, it can be placed between the vertebral bodies. Expandable disc replacement body 112 may be pushed or impacted into the disc space using insertion instrument 90 until it is fully seated with body 112 in the parallel starting orientation, such as a 0 degree angle between first wall 118 and second wall 120. A 0 degree or nearly 0 degree orientation at the time of insertion may allow for less force needed to insert expandable disc replacement body implant 112. A mallet can be used on the proximal end of insertion block 91 to provide placement of expandable disc replacement body 112 in the subject. FIG. 6C provides a rear view of the non-limiting example insertion instrument 90, where access holes 89 for drilling and inserting the bone screws may be seen. Drill guide 92, shown in one of the access holes 89, guides a drill bit to make pilot holes in the bone of the subject. Once the pilot hole is made, drill guide 92 is removed so a bone screw and driver can be inserted in the hole for bone screw alignment into the pilot hole. Lock lever 94 may then be turned to release the implant after all the bone screws are placed.

According to one method of use in surgery, a surgeon first removes an intervertebral disc from between two adjacent vertebrae of a patient. Then, expandable disc replacement body 112 of spinal fixation system 100 described above may be placed using insertion instrument 90 between the two adjacent vertebrae, such that first bone-screw receiving section 128 is adjacent the superior of the two vertebrae and second bone-screw receiving section 150 is adjacent the inferior of the two vertebrae. In some configurations, insertion instrument 90 is a separate instrument from the angle-adjustment instrument or disc replacement holder 93, described below. In other configurations, the insertion instrument is the disc replacement holder 93, such that disc replacement holder 93 implants expandable disc replacement body 112 into the spine of a subject and disc replacement holder 93 may also adjust the angle.

Referring to FIGS. 7A, 7B, and 8-10, a non-limiting example of an angle-adjusting disc replacement holder 93 is shown. Disc replacement holder 93 may be used to adjust the angle of expandable disc replacement body 112. Disc replacement holder 93 may also releasably engage with disc replacement body 112 via pins 95 through pin holes 151, which are visible in FIG. 7 when the superior plate is shown as a transparent outline. Pins 95 may allow for disc replacement holder 93 to apply torque to disc replacement body 112 to open disc replacement body 112 to the desired angle.

Pilot holes may be drilled into the superior and inferior vertebrae to aid in the insertion of the first through fourth bone screws into the vertebrae. A sounding rod may be inserted through the drill guide holes into the pilot holes. Once expandable disc replacement body 100 is placed between the two adjacent vertebrae, the first and second bone screws may be screwed into the superior vertebra through first and second openings 138, 140, respectively, and the third and fourth bone screws may be screwed into the inferior vertebra through third and fourth openings 159, 161, respectively. First and second openings 138 and 140, and third and fourth openings 159 and 161 may be oriented at an angle from the axis of expandable disc replacement body 100, such as between 10-75 degrees from the horizontal. In some configurations, the angles for first and second openings 138 and 140 may be different from the angles of third and fourth openings 159 and 161. In a non-limiting example, first and second openings 138 and 140 may be oriented at a 30 degree angle and third and fourth openings 159 and 161 may be oriented at a 10 degree angle for bone-screw insertion. One skilled in the art will appreciate that any selection of angles may be used.

The drill hole may be selected to be marginally larger than the planned bone-screw head diameter, which allows for a drill guide to be first inserted and a pilot hole power or hand drilled. Then a drill guide cannula may be removed and the screw may be inserted through the hole. In some configurations, a tap could be used prior to screw insertion for non-self-tapping screws. The minimal tolerance between the screw and the holes in the inserter instrument, such as insertion instrument 90 described above, my serve to guide the screw into the intended trajectory. Screw guidance may be a consideration when the device uses a dual-threaded screw, with a bone thread and a metal thread. These "locking" screw forms may require entering the plate at a precise angle that allows their low-pitch metal threads to engage the threads machined into the plate. Any significant deviation from the intended angle may prevent the metal threads from locking and stop full seating of the screw. The metal thread is contained in the head of the screw and it has a lower pitch, such that it is intended to engage machined thread in the screw hole of the implant creating a "locked" screw that has mechanical properties similar to a fixed-angled device. Non-locked screw constructs fail by the individual screws losing bone-screw friction, or purchase, over time and then backing out individually. Locked screw constructs, however, are a stronger construct that is less prone to failure through loss of fixation. This is especially true in bone of diminished quality, like that seen in elderly patients with osteoporosis.

After the first through fourth bone screws are in place, expandable disc replacement body 112 is effectively locked between the two adjacent vertebrae. At this point, disc replacement holder 93 can be used to achieve various angles between first wall 118 and the second wall 120 of expandable disc replacement body 112. This may be performed by expanding disc replacement body 112 by pushing on a thumb pad 96, which opens the implanted disc replacement body 112 to the desired angle. By pushing down on thumb pad 96, upper lever arm 21 may pivot on fulcrum 22 and raise the implant proximal portion 23 of upper lever arm 21, thus expanding expandable disc replacement body 112. Expansion ratcheting mechanism 24 may provide feedback to the surgeon regarding the amount of expansion based upon the resistance to pushing and the tactile feedback from progressing through a number of clicks of ratcheting mechanism 24. Ratcheting mechanism 24 may also prevent an over-expansion of expandable disc replacement body 112 by stopping at a maximum angle of expansion. The ratcheting mechanism 24 can be driven by applying force to a thumb pad 96 or by a screw or crank mechanism, and the like, or by any other mechanism capable of providing a metered expansion. The angle, which may be set by the surgeon at any desired angle, can then be locked in place by pulling back on trigger 97. Locking mechanism 114 on disc replacement body 112 may then be used to lock expandable disc replacement body 112 at the desired angle using locking screws 184 and 284 as described above.

Instruments used to facilitate the implantation of a device in accordance with the present disclosure may be simplified in construction, to permit single use production, which may enable the ability to sterilize the instrument set centrally, prior to delivery to the end-user. Since the cost and resources used to sterilize on-site by the end-user are significant, a single use configuration may provide for substantial cost savings for an end-user. This is especially beneficial in ambulatory surgery center settings, which have limited sterilization equipment on site. An instrument kit may also be single use, or could be reused while still sterilized centrally and provided to the end-user in a sterilize package.

In one configuration a kit is provided, which includes instruments that can be fabricated using methods and materials suitable for the intended function but costing a sufficiently low price to make and assemble, so as to allow one-time use. The disc replacement holder that drives the lordosis correction, can be simply a T-shape rod that is inserted horizontal into the anterior aspect of the disc replacement body 112 and then rotated into a vertical position, which in doing so creates a specific amount of lordosis correction. The final correction achieved can be pre-known to the surgeon and the surgeon can have multiple sizes to choose from to fit different footprints of the device and intended final degrees of lordotic angulation of the device. A simplified lordosis adjusting tool, along with a simplified version of the inserting instrument, can be manufactured and sterilely packed for single use, which obviates the need for cleaning and sterilization between uses when a non-disposable configuration of these two instruments is used. Sterilization is a costly process and each round of use and sterilization, increases the chance of incomplete sterilization and/or wear of the instruments. In a version of the kit for spinal surgery that enables use of disposable instruments, including a disc replacement holder that has the T-shape configuration, grooves can be cut into the surfaces of the disc placement body that guide the rotation and block over rotation of this T-shaped end of the instrument, such that the instrument is guided into a final vertical position that results in the intended amount of lordosis correction. A handle can be applied to this device that is torque-limited, which prevents over-expansion beyond a degree of lordosis that exerts a force on the upper and/or lower vertebra that risks fracturing the bone.

In some kit configurations, an insertion instrument may be configured to insert the expandable disc replacement body into a spine of the subject. In the kit, at least one of the insertion instrument and the adjustment instrument can be manufactured and sterile packed for single use or reused with the instrumented being sterilized by the end user or by the manufacturer, who may re-sterile and pack the instrument for its next use, obviating the need to sterilize the part at the end user's location. The simplistic design of the instruments needed to perform the insertion and fixation of this device may provide benefits in settings like an ambulatory surgery center, where apparatus for sterilizing surgical instruments is often very constrained. Kits containing all of the instruments needed to perform the operation could come as a single sterile-packed set for single use or reusable.

In some configurations, the anterior flanges may include cut-outs centrally to allow for use of a standard Caspar pin distractor system, such as for the cervical spine intended devices. The Caspar system is a commercially available system that uses pins screwed into the anterior and central portion of the vertebral body above and below the disc space that are then connect to a ratcheted expansion device that can be opened until the disc space is adequately distracted. This disc distraction facilitates disc preparation, as it is easier to see and work inside a distracted vs collapsed disc. It also indirectly decompresses the spinal canal and the neuroforamen, because opening the disc space, increased foraminal height and puts loose or buckling sponal ligaments on stretch. Using a Caspar pin distractor is a very common method for performing anterior cervical discectomy and fusion (ACDF), which may be facilitated by the cut-outs.

In some configurations, bone graft may be used with expandable disc replacement body 112. A user may push on the proximal end of bone graft pusher 98, which includes pusher head 99 with bone graft placed on the end facing expandable disc replacement body 112. Pusher head 99 then deposits the bone graft into the cavity of expandable disc replacement body 112.

Figure 1D:
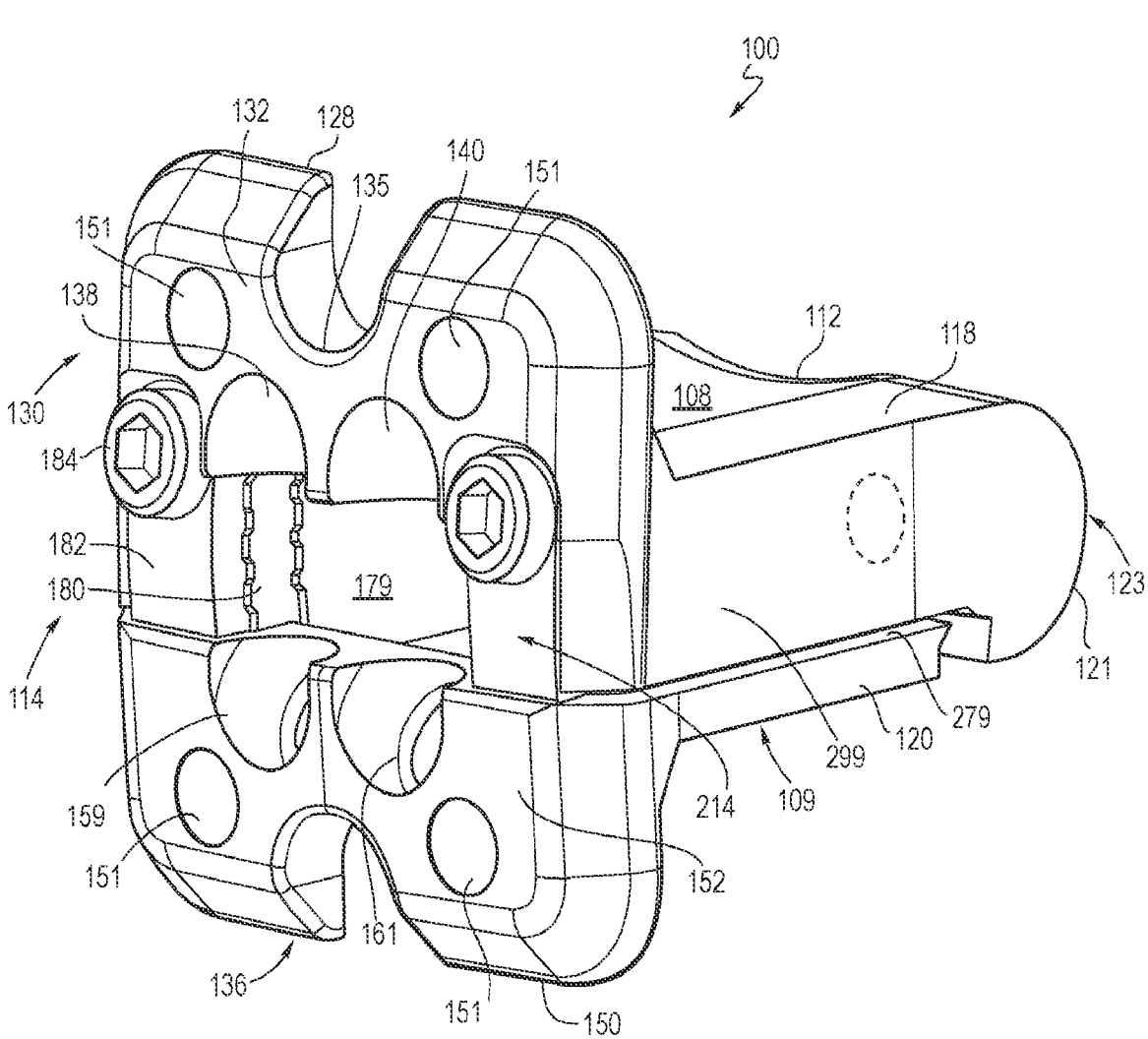
FIG. 1D is a front perspective view of one configuration of an expandable disc replacement body with a side wall for housing bone graft material in an interior volume.

Referring to FIG. 1D, in some configurations, liquid or flowable bone graft material may be used and a sidewall 299 may be used to create an interior volume for the bone graft material to prevent leakage or seepage from the interior volume. In some configurations, an elastic membrane may be affixed to the inner margins of first wall 118 and second wall 120, such that as the angle between the walls is increased, the membrane becomes progressively taught. The membrane's function may be to create a closed space within the central portion of the device that borders a bone graft chamber, defined by first space for receiving bone graft 126 and second space for receiving bone graft 149. The membrane can hold flowable bone grafting material in that central location of the device. Flowable bone grafting material, includes but is not limited to demineralized bone matrix paste, ceramic paste (calcium triphosphate, and the like) or semi-solid or liquid osteoinductive or osteogenic agents, such as bone morphogenic protein-2, and the like. Flowable bone grafting material may be used to serve as the biological substrate that initiates the fusion process between endplates 108 and 109 of the instrumented vertebrae, within the central confines of spinal fixation system 100. The typical consistency of a flowable bone graft is that of a paste (like toothpaste). At this viscosity, it can be injected through a reasonably narrow gauge (such as a 19 gauge or less) needle or cannula. The elastic membrane may be made of a flexible material that may be biocompatible, such as silicone, or polyurethane, and the like. The elastic membrane may be, translucent or transparent to provide for visibility of the bone graft content or surrounding anatomy.

Figure 1E:
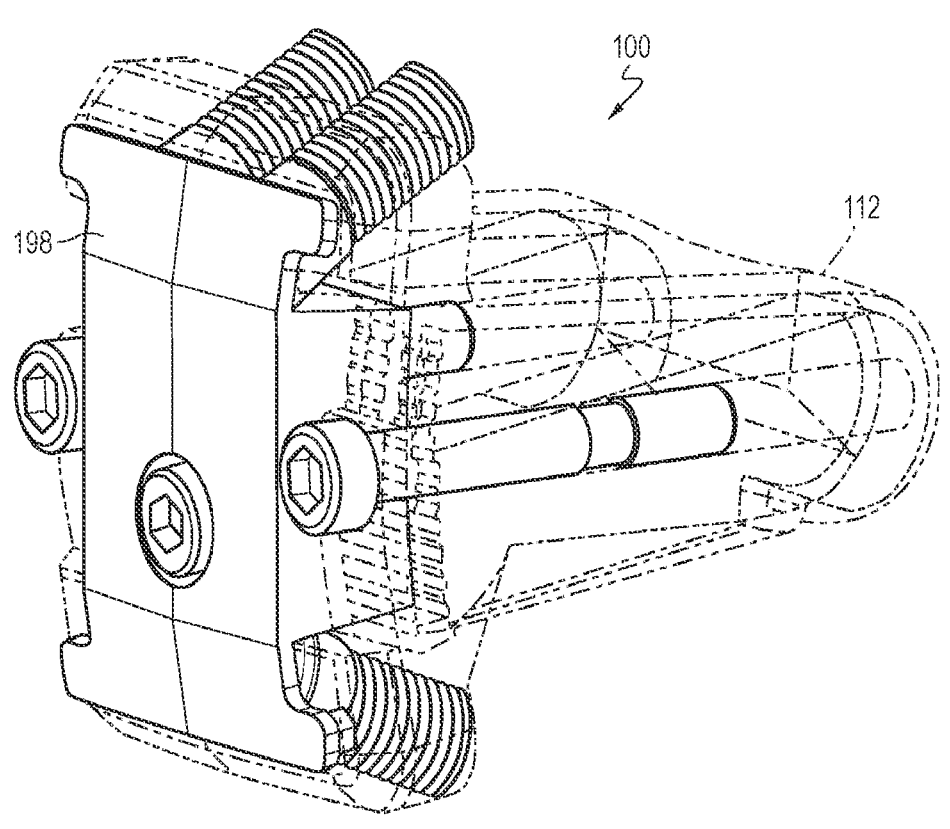
FIG. 1E is a front perspective view of one configuration for a spinal fixation system of FIG. 1A with a cover cap.
Figure 2:
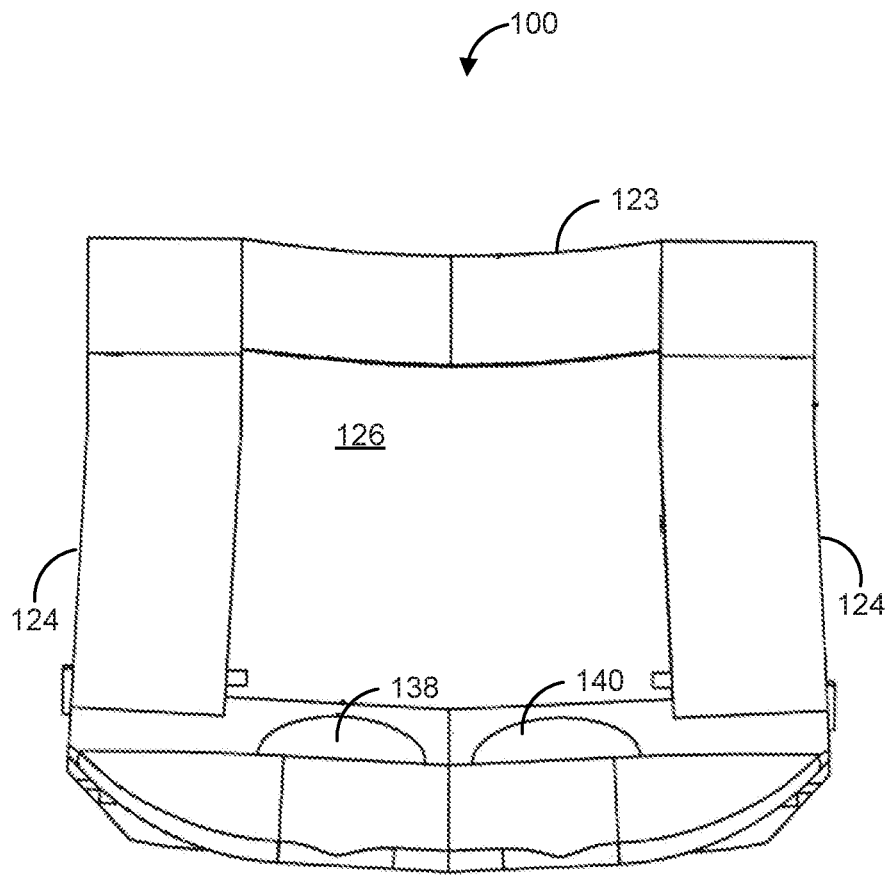
FIG. 2 is a top plan view of the spinal fixation system of FIG. 1A.
Figure 3:
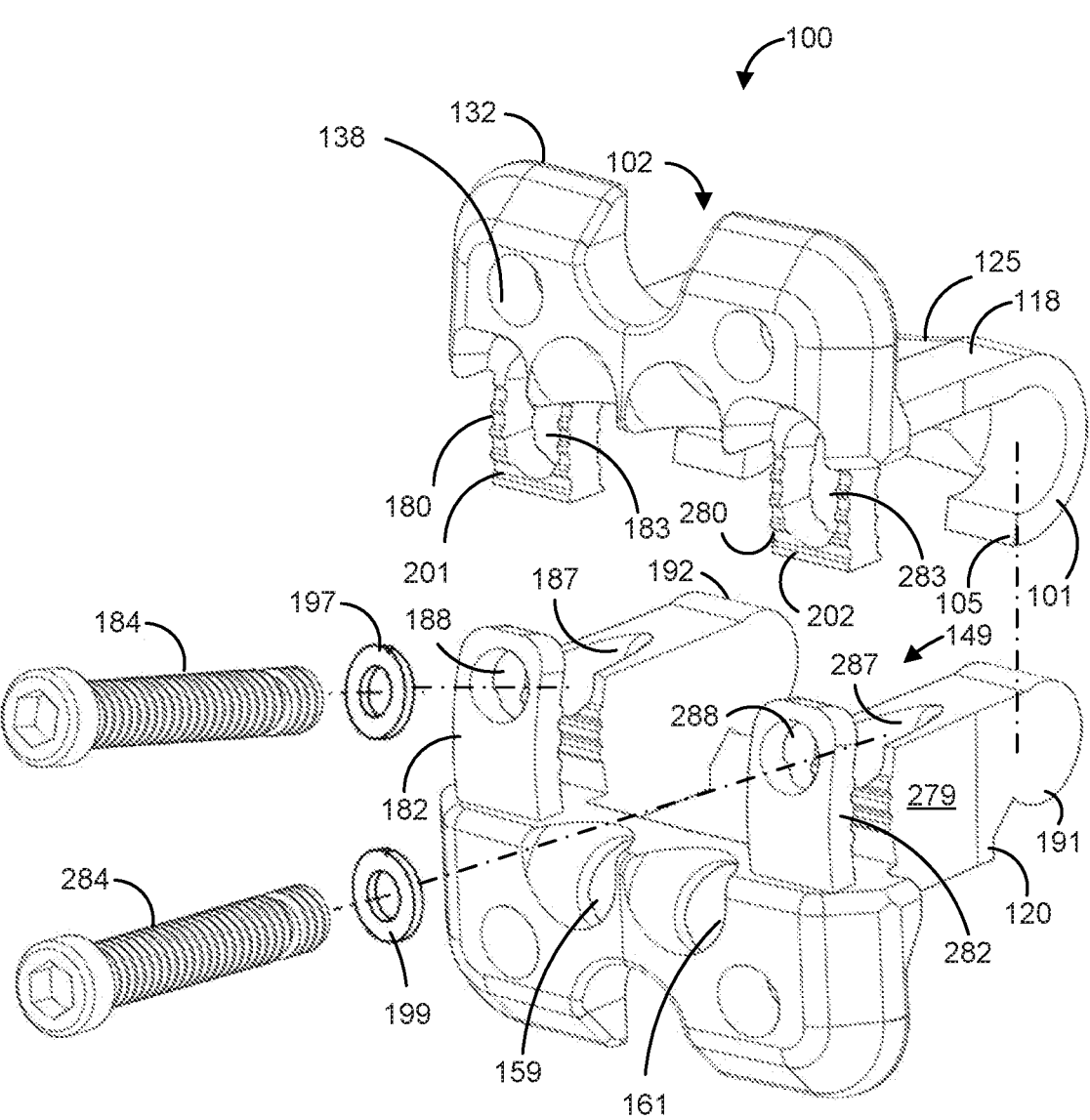
FIG. 3 is an exploded perspective view of the expandable disc replacement body of FIG. 1A.
Figure 4A:
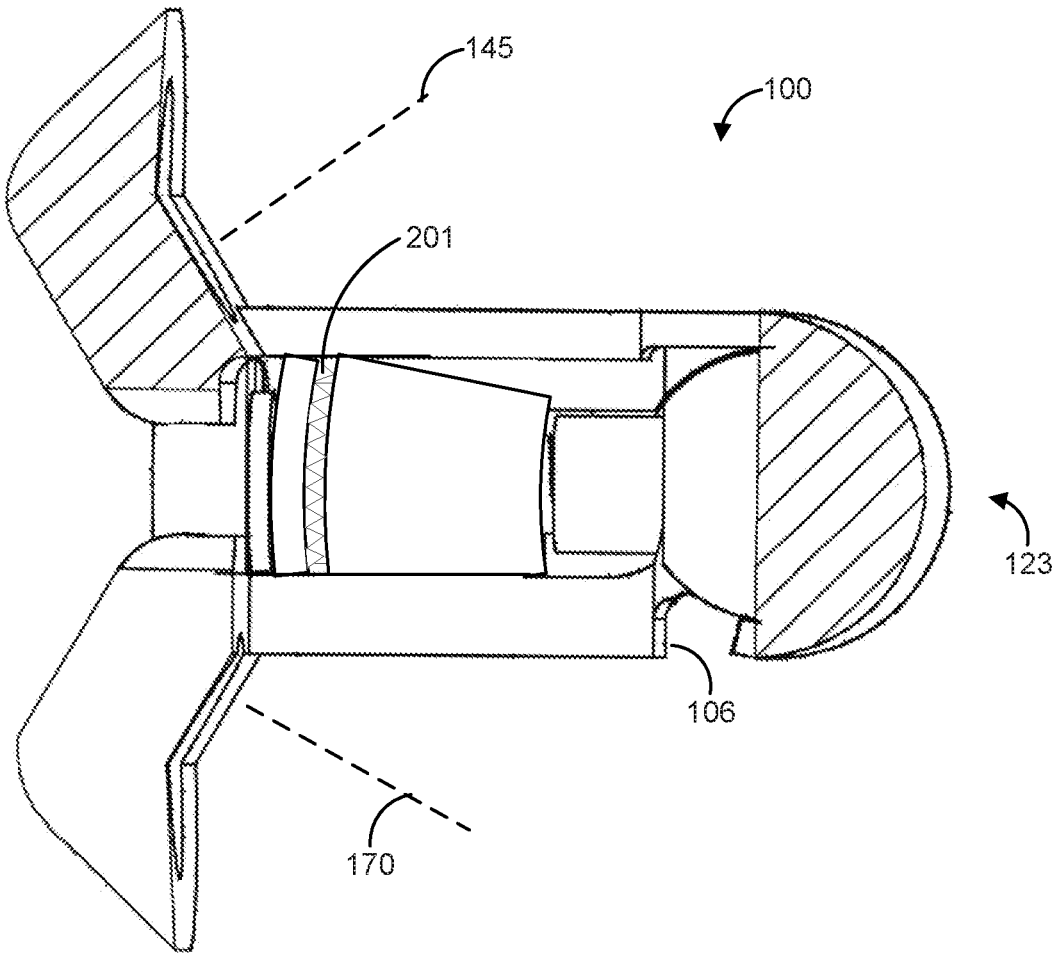
FIG. 4A is a side view of the expandable disc replacement body of FIG. 1A.
Figure 4B:
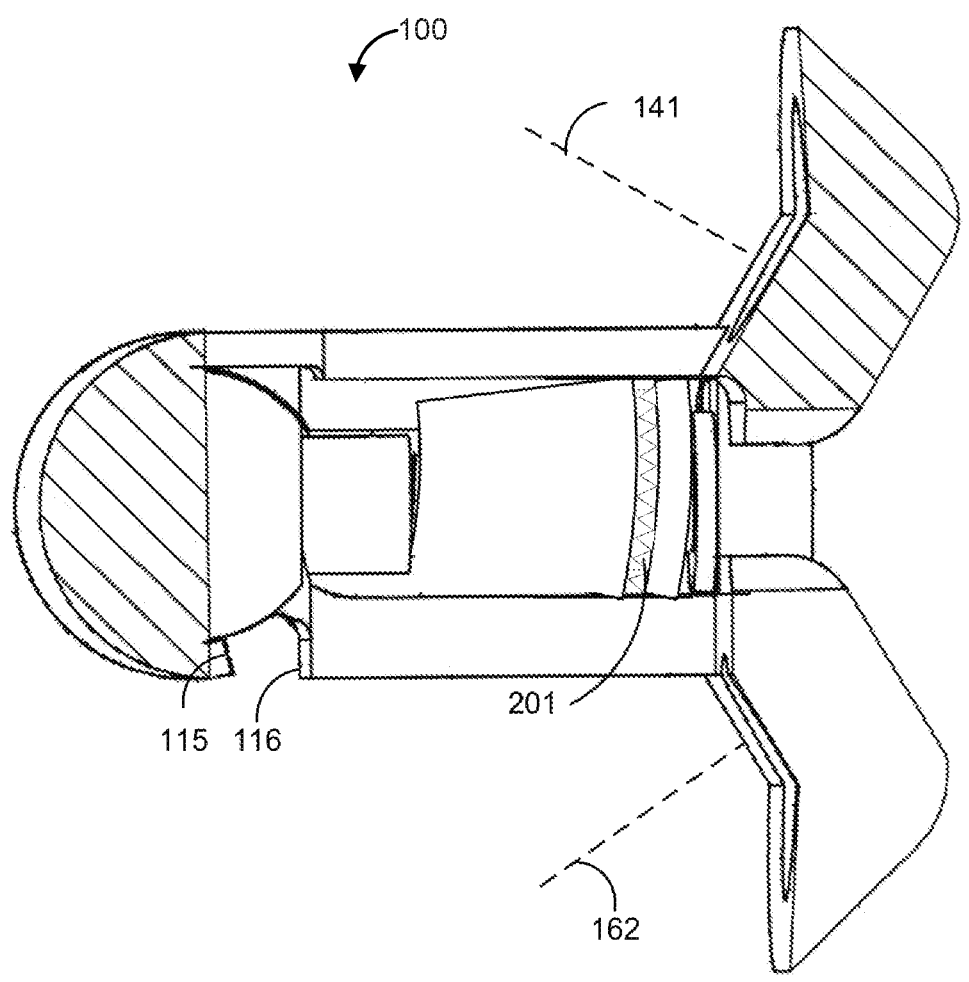
FIG. 4B is an opposing side view to FIG. 4 of the expandable disc replacement body of FIG. 1A.

Referring to FIG. 1E, in some configurations a cover cap 198 can be used to cover the anterior access point to the central graft cavity. This cover cap 198 may be sized and shaped to fill the space 126 between the first and second walls 118 and 120 respectively, with sufficient coverage to prevent leakage of paste like grafting material. The cover cap 198 may also prevent liquid bone graft substitute material from leakage. In some configurations, the cover cap 198 may provide coverage to the anterior surface of the bone screws, to prevent unintended back out. Effacement between the upper and lower walls, may also further prevent compression and closure of the device. In some configurations, anterior flanges on the cover cap 198 may engage the fixation points on the anterior surface of the implant to prevent subsequent extension/opening of the implant once in final conformation. A cover cap 198 may not only provide an anterior wall to the central graft cavity, it may also provide added structural stability.

Referring again to FIGS. 1D, 7A, 7B, and 8-10, in some configurations, bone graft pusher 98 may be replaced by a needle, cannula, syringe, or other device for introducing flowable bone graft. The elastic membrane may contain a connector, manifold, or self-sealing area that allows for the introduction of the needle, cannula, or syringe into the central cavity of the device, without producing a permanent defect in the membrane. The device used to inject the flowable graft can be calibrated and marked to identify specific volumes of material injected that would correspond to the specific volume within the central cavity based on the selected height of the cage and angle of opening that has been locked. In some configurations, the cage can be placed without graft in the central cavity. In some configurations, the cage may be pre-loaded with a select amount of bone graft prior to implantation. The conformation of the cage may be adjusted and then locked into place via the bone-screws and angle locking screws 184 and 284. When there is a known defined central volume, the corresponding amount of flowable graft material can be injected to fill the central cavity and be contained on all sides by either vertebral endplates 108 and 109 above and below, the lateral sides 124, distal end 123, or the anteriorly affixed elastic membrane.

The graft may be inserted to fill a specific volume. In configurations when the volume is fixed, additional graft can be inserted with additional pressure applied to the flowable bone graft introducer, causing contact between upper endplate 109 and lower endplate 109, replicating compression on a solid bone graft or at least reducing, if not eliminating, gaps between endplates 108 and 109 and the flowable graft. The snug fit of the device, between the adjacent vertebrae and distal end 123, lateral sides 124 along the area of lordotic angle locking screws 184 and 284 on the sides and the anterior membrane, as well as the preserved lateral annulus, may act as rigid constraints against extravasation of the flowable graft. The elastic nature of the membrane may also provide some relief against over-fill of the space.

In some configurations, the elastic membrane prevents accidental release of a flowable bone graft fluid to adjacent tissues. These accidental contacts provide no clinical benefit to the patient, and may induce adverse reactions in some patients. At best, an accidental contact would yield no adverse response, but they can produce very serious complications, which include soft tissue swelling, difficulty breathing, retrograde ejaculation, seromas and other hyper-inflammatory adverse reactions. Some bone graft substitutes, like INFUSE (Medtronic, Inc) are processed in the surgical field by adding a liquid to a dry sponge (acellular collagen). The elastic membrane can allow for the dry sponge to be packed into the central portion of the cage prior to implant insertion and then the needle or cannula can be inserted through the membrane to deliver the specified amount of fluid to the dry sponge. Injection of the fluid after implantation may avoid pieces of a pre-wetted sponge from breaking away during implantation and contacting the surrounding tissue. The addition of fluid to any sponge also causes a natural expansion that further fills the cavity and reduces gapping between the graft and vertebral endplates 108 and 109, which may provide for greater fixation and clinical efficacy of spinal fixation system 100.

In one non-limiting example, the proposed method would solve a serious problem related to the use of BMP-2 in anterior spinal surgery, especially in the cervical spine. BMP-2 is very inflammatory, it induces a vigorous local inflammatory response in any tissue or location in the body that comes into contact with BMP-2. All current methods for inserting BMP-2 into the disc space, require that the BMP-2 be placed as a pre-wetted sponge loosely into the central portion of an interbody cage. As the cage is impacted, liquid and sometimes even pieces of the sponge may be dislodged and come in direct contact with the local surroundings. In the cervical spine this has created anterior soft tissue swelling so severe that it can produce difficulty breathing. This is such a serious complication that the FDA has placed a warning against the use of BMP-2 in the anterior cervical spine. The elastic membrane described above may reduce or eliminate the chance of accidental application of BMP-2, bone graft, or other fluids placed in the membrane to the areas local to the spine.

Bone growth may be promoted by surface treatments made to spinal fixation system 100. Surface treatments may include, but are not limited to, plasma coating, 3-D porous metal construction of all or some of spinal fixation system 100 (such as 50-600 micron pores, or pores of any other size), hydroxyapatite coatings, metal abrasion, reductive techniques that create pits in the metal (such as between the 30-600 micron diameter, or any other size), and the like which encourage bone in-growth or on-growth. In non-limiting examples, surface treatments may be made to portions of expandable disc replacement body 112, such as first wall 118 or second wall 120, or may be made to the threads of locking screws 184 and 284.

In some configurations, a calibrated adjustment for changing the angle using disc replacement holder 93 is provided. Disc replacement holder 93 may be rigidly and releasably connected to expandable disc replacement body 112 and allows for changing the angle between first wall 118 and second wall 120 to a specific degree of lordotic angulation. A calibrated adjustment may be provided by an angle guide attached to disc replacement holder 93. In some configurations, the angle guide is ratcheting mechanism 24. The angle adjustment guide may act similar to a ratcheting mechanism, as discussed above, where the angle guide indexes disc replacement holder 93 corresponding to 0.5 degree, or 1 degree, or other selected angle amount of expansion between first and second walls 118, and 120. In some configurations, the angle guide is not confined to angles of integer value, nor at largely spaced intervals (i.e., 3.2, 3.4, 3.6, 3.8 degrees), as the angle guide may be configured with any set angles at predetermined locations. An advantage to an angle adjustment guide coupled to disc replacement holder 93 is to avoid the limitations of conventional devices. Conventional devices include bulky angle adjustment mechanisms within the implanted device, which occupies space in the device that can be used for better purposes, like bone grafting or reinforcing the structural strength of the device.

Changing the angle using an instrument, such as disc replacement holder 93, that is external to an implant, such as expandable disc replacement body 112, would optimize the functionality of an implant since an external implantation instrument can be as strong as it needs to be to set the angle. An internal device, however, may be limited to the diameter of the screw and screw material used to drive the lordosis producing mechanism. In some configurations, disc replacement holder 93 may be torque-limited, such as being set at a torque that is unlikely to cause the device to fracture or plow into the vertebra above or below based on bone mineral density or other commonly measured biomechanical properties of the spine being implanted. In some configurations, disc replacement holder 93 may include clear space in the central portion of the device that can be used as a window for inserting solid or flowable graft and a large central cavity for this graft to promote solid fusion between the adjacent vertebrae.

In some configurations, disc replacement holder 93 may allow for both adjustment of lordosis angle and also for achieving a specified height through vertical expansion of expandable disc replacement body 112. Disc replacement holder 93 can engage a mechanism that allows for adjustment of the angle between first wall 118 and second wall 120, and also may engage a second component of expandable disc replacement body 112 that allows for vertical expansion of expandable disc replacement body 112, such that the height of the device may be increased in-situ, during implantation, or after implantation. Increasing disc height increases the volume of the neuroforamen and thereby indirectly, but often clinically effectively, decompresses the exiting nerve root.

In one non-limiting example, a vertical expansion may be provided by posterior hinge 121, between first wall 118 and second wall 120, being a cam-shaped structure. In some configurations, a lower wall (not shown) may be a lower facing wall that couples to lower endplate 109, a middle layer that acts as the base for the lordosis correcting mechanism and a top wall (not shown) that would engage upper endplate 108 and mark the upper limit of the lordosis correcting first wall 118 and second wall 120. The implantation instrument or the angle adjusting instrument would first engage the lower and upper walls and apply a pure axial force that acts to vertically translate the upper wall from the lower wall. This would cause posterior hinge 121 to slide up a flatter lower portion of the cam, and then engage the upper portion that may include a semi-circular shape that allows for in-situ lordosis correction. The disc height gain may be locked in place by engaging ratchets that prevent expandable disc replacement body 112 from collapsing to its native height or by a locking screw mechanism as described above, or by other mechanisms such as snap fit. A snap fit may include concentric semi-circles snapped over each other, such that it is not possible without extra-physiological loads to collapse expandable disc replacement body 112. The disc height lock may prevent motion between the layers. The angle-adjusting instrument, such as disc replacement holder 93, may set the lordosis angle as described above.

Angle adjustment instruments may also use a turn-dial, a thumb press, a levering effect, or a combination thereof. In some configurations, the angle adjustment instrument may be inserted in a horizontal configuration and rotation to the vertical may result in a preset amount of angular correction. An angle adjuster instrument may have an integrated torque meter, or torque limitations, that allows the surgeon to understand the amount of force and pressure they are applying to the vertebral endplates above and below and for the surgeon to make an informed decision whether the additional degree of angular correction is worth the risk of bone failure with higher torques applied. In non-limiting examples of torque limitation configurations, the torque limit can be absolute, or may be adjustable. An adjustable configuration may provide for the surgeon to adjust the maximal torque enabled by the angle adjuster instrument during the process of inducing an angular correction. This may allow the system to be customized to various patients, from those with good bone quality (e.g. would be able to take higher torques, force, pressure, and the like) to those with poorer bone quality. This ability does not exist in current practice, and as a result excessive torque when applied to patients with diminished bone quality can lead to failure of the bone and loss of correction and/or subsidence in lieu of angular correction. In some configurations, the angle adjuster instrument may record and display the current torque. Alarms may be included which indicate to the surgeon that a threshold torque has been reached.

In some configurations, the angle may be prevented from slipping by initial contact of surface features 201, 202 before the locking screws 184 and 284 are tightened down. Once the final position of expandable replacement body 112 is achieved, disc replacement holder 93 may be removed along with pins 95, and locking screws 184 and 284 may be tightened down. Locking screws 184 and 284 may include treads or teeth designed to engage with second arm apertures 188 and 288 to prevent backing out. Washers 197, 199 may also be lock washers that prevent backing out.

Locking screws 184 and 284 that "lock" the walls at the preferred angle, may include anti-backout mechanisms, such that prevent locking screws 184 and 284 from backing out. Backing out would allow for the angle to slip and no longer lock the preferred angle between first wall 118 and second wall 120. In a more severe case, locking screws 184 and 284 could fully back out and partially or fully disengaging from the device without the use of anti-backout mechanisms, which could produce pressure on adjacent structures (like the esophagus) or yield a free body that could migrate to other parts of the patient. In some configurations, the anti-backout mechanism may be a locking tip to the screw, such that when it is fully inserted it engages a locking washer or the like at its tips, which prevents the screw from backing out from this position. In some configurations, the anti-backout mechanism may be a deformable washer lock, such as a Nitinol gasket, or wire, and the like that is located at the insertion point of locking screws 184 and 284. As locking screws 184 and 284 are fully seated, the deformable washer lock may deform until the heads of locking screws 184 or 284 clear the deformable washer lock and then the deformable washer lock may rebound to cover the screw heads to prevent backout under normal physiological loads. In some configurations, the anti-backout mechanism may be a separate component that is screwed in or impacted onto expandable replacement body 112 that rigidly connects to expandable replacement body 112 and covers the heads of locking screws 184 or 284 to prevent back-out. In some configurations, extreme torque may be used to intentionally release the lordosis mechanism in case of revision.

Figure 11A:
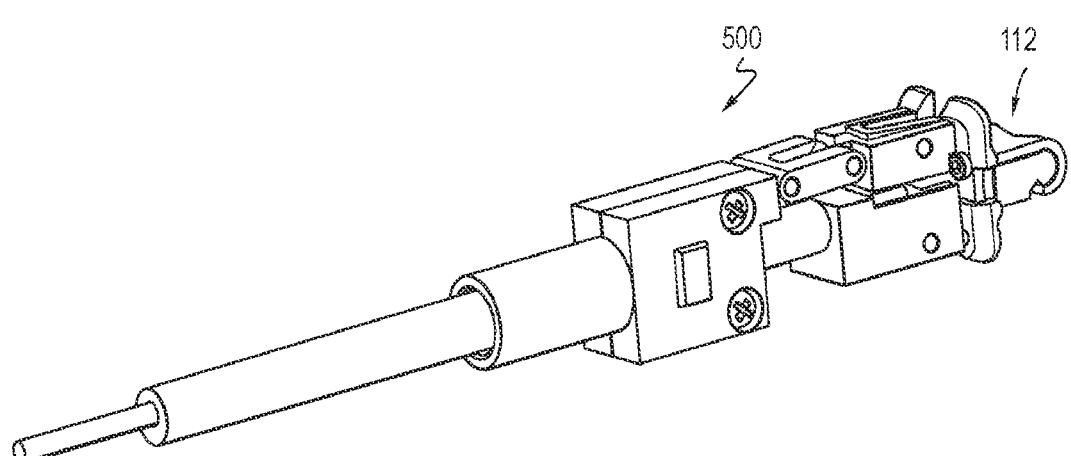
FIG. 11A is a rear perspective view of another non-limiting example disc replacement holder.
Figure 11B:
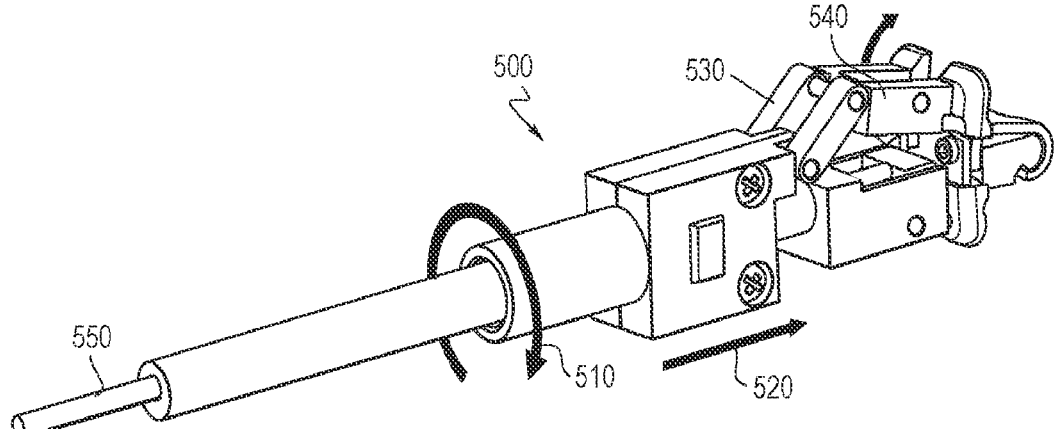
FIG. 11B is a rear perspective view of the non-limiting example disc replacement holder of FIG. 11A showing the disc replacement holder partially opening the expandable disc replacement body of FIG. 1A.

Referring to FIGS. 11A and 11B, another non-limiting example of a disc replacement holder or opening device 500 is shown. Opening device 500 may releasably engage with expandable disc replacement body implant 112 in the same manner as described above for disc replacement holder 93. To open expandable disc replacement body 112, a user may first turn a drive shaft 510, which may have internal threads to drive it forward towards disc replacement body 112. A shaft may spin freely inside drive block 520, which is pushed forward by drive shaft 510. Drive block 520 then pushes up on superior block 540 via push arms 530. With the connection made between superior block 540 and the superior plate of disc replacement body 112, disc replacement body 112 may be pried open to adjust the angle of lordosis. Opening device 500 may be narrow enough in size for a driver to access lordosis locking screws 184 and 284 discussed above. A graft pusher 550 may be used to push a graft into the implant as described above.

Figure 12A:
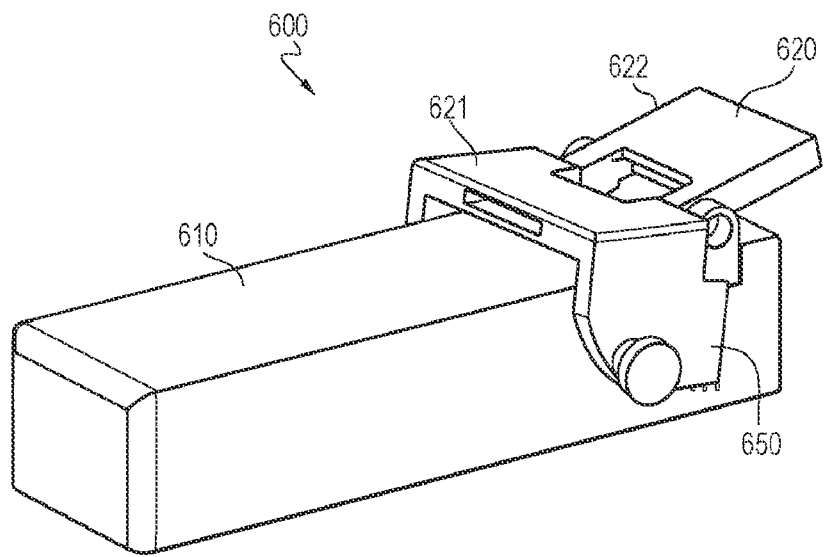
FIG. 12A is a rear perspective view of one configuration for a cutting guide for use with the present disclosure.
Figure 12B:
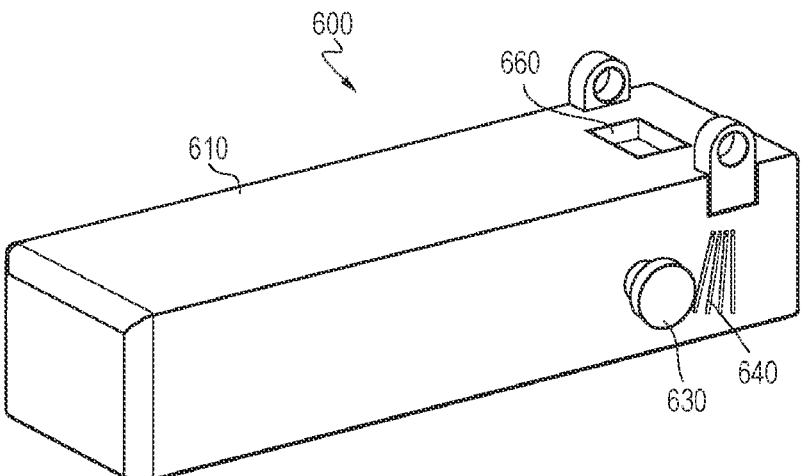
FIG. 12B is a rear perspective view the cutting guide of FIG. 12A showing the base of the device.

Referring to FIGS. 12A and 12B, a non-limiting example of a cutting guide 600 is shown. Base 610 may be coupled to blade sleeve 620, which includes openings for creating cuts, such as two openings as depicted with first opening 621 and second opening 622. First opening 621 may be used to cut the graft to match the lordosis of expandable disc replacement body implant 112. Second opening 622 may be for cutting the superior anterior corner of the graft to create a chamfer to reduce the opening height of expandable disc replacement body implant 112 for letting the graft pass through. FIG. 12B depicts base 610 without blade sleeve 620 to show pivot mount 630 and cutting angle detents 640. Cutting angle detents 640 may provide feedback to a user on the angle of blade sleeve 620 by interacting with arm 650, or may provide for fixing the angle of blade sleeve 620 at a defined angle during use. The angle of blade sleeve 620 may set the angle of lordosis for the first cut using first opening 621. A pocket for holding graft, such as the bone graft discussed above, may be provided with pocket 660.

In some configurations when using cutting guide 600, graft may be pushed in from the anterior side of expandable disc replacement body 112, which may allow for the graft to drop into the inferior plate after it clears the anterior flange. A chamfer may be provided in the hinge to reduce the angle needed for the disc replacement body 112 to open to allow for placement of the graft. During implantation, expandable disc replacement body 112 may be "over-lordosed" temporarily to allow a solid bone graft to clear the anterior surface of body 112 and be inserted into the central cavity. This over-lordosis can be reversed after the graft is in place, which effectively compresses or at least minimizes gapping between the vertebra above and below and the bone graft. Bones heal better in compression and with better apposition between the graft and the host bone. In a non-limiting example, the over-lordosis is between 1-2 degrees greater than the final implanted lordosis.

In some configurations, a solid bone graft may be used. Cutting the solid bone graft may allow for standard sized grafts to be stored, thus reducing inventory expense and logistical challenges. The standard sized graft can be passed sterilely into the surgical field once the footprint size is selected. The graft can then be loaded into place and once the final lordotic angle is selected, it can be cut to the proper size and chamfer. In some configurations, the bone graft may be inserted into a space that has been temporarily made larger than the final resting position through the "over-lordosis" mentioned above. In some configurations, the graft can be made with less cortical bone and more cancellous bone. Cancellous bone is more likely to incorporate with, and faster to incorporate with, native bone than cortical bone. Cortical bone, however, may be needed for standard structural allografts, as they may be malleted into place with force that would crush normal cancellous allograft. Fresh-frozen allograft may be used and these grafts may include superior fusion potential. Conventional frozen allograft requires a thaw time that can be several minutes in length, which may be a nuisance to use intraoperatively since what size may be needed may be unknown until after the procedure has begun. In such a situation, the nurse would need to go to the freezer to obtain the required size, return to the procedure room, thaw the graft, and then it may be inserted. Improperly sized and thawed graft cannot be re-frozen. With a standard size graft, these delays may be avoided as long as a user knew the planned footprint preoperatively, or once the footprint is selected intraoperatively.

Figure 13:
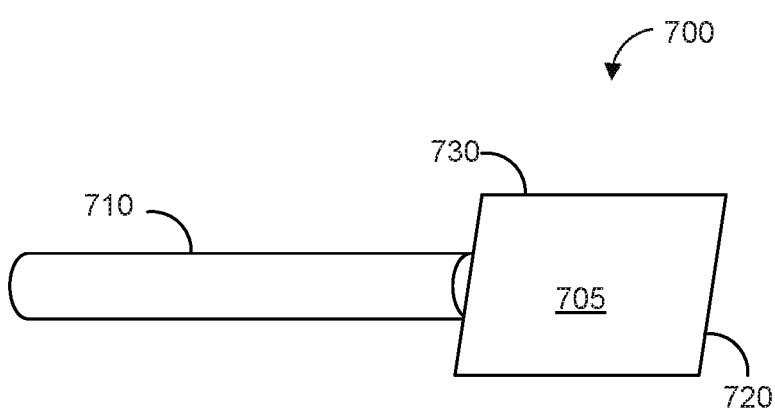
FIG. 13 is a side view of a non-limiting example trial device for use with the present disclosure.

Referring to FIG. 13, a non-limiting example trial device 700 is shown. In some configurations, a trial device 700 may be used to determine the size or appropriate angle of an implant for a subject. Trial device 700, which may include integrated insertion shaft 710 that can rotate the central portion of trial device 700 in some configurations, may be inserted into the subject with a planar appearance at the location where the implant is desired to be placed. Trail device 700 may include a width 720 that may be used to determine a height for an implant in the spine upon rotation, and a depth 730. In a non-limiting example, trial device 700 is around 3 millimeters tall. In some configurations, trial device 700 is sized to fit of the foot-print of the implant location in the subject. For different sized implants there may be a corresponding trial size. Once the proper size and location in the subject is select, the central section may rotated clockwise using shaft 710 until it solidly engages with the endplate above and below. Trialing may be performed with the disc space in distraction from a commercially available disc space distractor like the Caspar pin set or in its native position. To determine height, a single rotating distractor paddle 705 may be used, such as a distractor that is 9 mm in width for C-spine and wider for T-spine and L-spine implants. Distractor paddle 705 may be rotated to 90 degrees in order to determine the size of the disc replacement body, such as rotating a 9 millimeter width 720 to determine that the disc space would accept a 9 millimeter posterior height of the expandable disc replacement body 112. In another non-limiting example, if 8 millimeters would be appropriate for the space, a 9 millimeter distractor paddle 705 would rotate less than 90 degrees, with less degrees of rotation equating to less and less normal vertical expanse.

In some configurations, rotating shaft 710 of trial device 700 can have ratchets or gears and the like such that as it rotates to a specific arc of rotation that results in trial device 700 achieving a preset vertical height (such as 5 mm., 6 mm., 7 mm., and the like). The ratchet may click or provide some manual/tactile feedback to a user regarding the rotation. In some configurations, there may be a gauge that records the current vertical (normal to the endplate plane) height. Different disc heights may be tested by a single device for a single footprint. The magnitudes of height disclosed above are non-limiting examples of a device intended for the cervical spine. Larger magnitudes of height may be needed for the thoracic spinous process (TSP) and lumbar spinous process (LSP). Alternatively, trial device 700 may be specific for only a single width 720 and depth 730 (i.e., footprint) and therefore specific for a single height where trial device 700 is rotated into the 90 degree position to determine height.

Trial device 700 could be located centrally or paracentrally. If paracentral, it may be located on one side as the device could be flipped 180 degrees and reinserted to test the other side. An advantage of a paracentral location is that the disc itself tends to have a concave upper shape, so that the vertical height in the middle may be greater than on the sides, but the lateral limbs of a device may engage the peripheral bone. Trialing the center could over-call the ideal height for an implant. This could lead to "over-stuffing" or inability to get the selected implant into final position.

In some configurations, trial device 700 could be used with multiple sizes that have the same shape as the intended implant in its planar conformation, such that a unique trial device is provided for each width, depth, height configuration in the system. A trial device 700 would be needed for each available disc height and foot-print. In a non-limiting example, 15 trials would be used if 3 footprints were used with 5 different heights.

The posterior aspect of trial device 700 may be rounded, either to the same arc of curvature as the implant or to a more wedged shape, such that it acts to help pry open the space to some degree as trial device 700 is inserted into the disc space to identify the best fit implant footprint and height. Trial device 700 may include a small anterior flange (not shown) on the upper and lower anterior aspects to prevent over-insertion, which could contuse the spinal cord. Such a flange may allow the surgeon to make sure that the lordosis angle is appropriate when fully inserted. It is common to have anterior osteophytes that need to be burred or otherwise thinned down prior to placing a fixation device anteriorly, to prevent implant prominence. Trial device 700 may include an internal hinge that can be opened similar to hinge 121 described above for expandable disc replacement body 112 of FIG. 1A, and this internal hinge may be calibrated so that the surgeon could know what footprint, height, and angle of lordosis may fit the disc space and may improve the disc height and lordotic angle of the native spine. Trialing is an important step towards preventing waste and increased cost from being forced to purchase implants that do not fit after they have been opened in the operating room. It also may enable pre-fixing a separate anterior stabilization plate to the expandable disc replacement body prior to insertion. It also may allow for a fresh-frozen standard bone graft of the proper footprint to be opened, thawed, and then cut in to proper size as described above, while the remaining steps of the expandable disc replacement body insertion/implantation technique are being conducted. This multi-tasking ability would significantly expedite the implantation technique, and reducing surgical time reduces complications and costs.

Thus, the invention provides spinal fixation systems, multi-level spinal fixation systems, and kits for spinal surgery. Furthermore, it will be appreciated by those skilled in the art that elements of the various embodiments described herein can be used in conjunction to achieve desired results. The specific embodiments illustrated are examples and are not meant to be limiting. In this regard, the embodiments illustrated herein may refer to use for anterior cervical spine surgery. However, the spinal fixation systems and methods of the present disclosure are useful over the entire spine. For example, the spinal fixation systems and methods of the present disclosure can be used at the thoracic or lumbar spine. Furthermore, embodiments of this invention can be inserted via lateral entry as opposed to the anterior entry. While the non-limiting embodiments of the present disclosure show an anterior cervical device that is applicable for all direct anterior use from C2 to S1 vertebrae, in the thoracic spine and lumbar spine, the spinal fixation systems of the present disclosure can be used as a lateral cage, that enters from the side and has the adjustment mechanism that can increase lordosis and/or correct coronal angulation (i.e., in scoliosis). Thus, the spinal fixation systems and methods of the present disclosure work beneficially from C2 to S1 vertebrae, with one difference being the scale of the expandable disc replacement body of the spinal fixation system.

The system and devices described in the present disclosure may be individually packed for sterility, or may be pre-packaged in small mated sets in a sterile, one-time use fashion. The used instruments may also be collected by the implant representative at the end of the case or returned by the hospital to the implant manufacturer on a periodic basis to allow them to be recycled and reused for additional cases.

Additionally, prior to the insertion of any of the described spinal fixation systems, a computer templating system can take specific measurements from preoperative imaging to define the native dimensions of the disc space (i.e., height, width, depth, and angulation between adjacent vertebrae) as well as global dimensions (i.e., height, depth, and angulation of a general spinal region). These dimensions can then be used to calculate a prescribed amount of correction (i.e., height and/or angulation degree) of each individual spinal fixation system, between multiple pairs of adjacent vertebrae, to achieve a desired global deformity correction. This prescribed correction can be multi-planar for both sagittal and coronal plane correction.

The present disclosure has described one or more preferred embodiments, and it should be appreciated that many equivalents, alternatives, variations, and modifications, aside from those expressly stated, are possible and within the scope of the invention.

The invention claimed is:

1. A kit for a spinal fixation system comprising:
(i) an expandable disc replacement body including a first wall, a second wall, a hinge connecting the first wall and the second wall, and a locking mechanism including a first arm coupled to the first wall, a second arm coupled to the second wall, and a first locking wall, wherein the first arm, second arm, and first locking wall are positioned between the first wall and the second wall,
(ii) an anterior plate configured to provide fixation for the expandable disc replacement body in a subject; and
(iii) an angle adjustment instrument, wherein an angle between the first wall and the second wall is adjusted with the angle adjustment instrument, and the angle can be locked in place at a time of implantation in the subject,
wherein opposite surfaces of the first arm engage the first arm between the second arm and the first locking wall to lock the angle in place.

2. The kit of claim 1 wherein the angle adjustment instrument includes a lever arm and a fulcrum for expanding the expandable disc replacement body.

3. The kit of claim 2, wherein the angle is continuously varied between a lower value of the angle and an upper value of the angle by movement of the angle adjustment instrument.

4. The kit of claim 2, wherein the angle adjustment instrument includes:
a ratcheting mechanism to provide tactile feedback to a user regarding an amount of expansion of the expandable disc replacement body.

5. The kit of claim 4, wherein the angle adjustment instrument is configured to adjust the angle to a higher angle as bone graft is pushed into the space in the expandable disc replacement body, and
wherein the angle adjustment instrument reduces the angle to a lower angle after the bone graft introducer is removed.

6. The kit of claim 4, wherein the ratcheting mechanism provides for 1 degree increments for the amount of expansion of the expandable disc replacement body.

7. The kit of claim 1, wherein the locking mechanism includes:
flexing the second arm to engage the first arm between the second arm and the first locking wall.

8. The kit of claim 7, wherein the hinge includes a threaded portion for receiving the locking screw.

9. The kit of claim 1, further comprising a second locking mechanism including:
a third arm coupled to the first wall,
a fourth arm coupled to the second wall, and
a second locking wall,
wherein the third arm, fourth arm, and second locking wall are positioned between the first wall and the second wall.

10. The kit of claim 9, wherein the second locking mechanism includes:
flexing the fourth arm to engage the third arm between the fourth arm and the second locking wall.

11. The kit of claim 1, wherein the spinal fixation system includes a surface treatment, and wherein the surface treatment includes at least one of a plasma coating, 3-D pores, a hydroxyapatite coating, metal abrasion, or metal pits.

12. The kit of claim 1, further comprising an insertion instrument configured to insert the expandable disc replacement body into a spine of the subject.

13. The kit of claim 12, wherein at least one of the insertion instrument and the adjustment instrument are manufactured and sterile packed for single use.

14. The kit of claim 12, wherein the expandable disc replacement body includes a first bone-screw receiving section at a proximal end of the first wall, and a second bone-screw receiving section at the proximal end of the second wall.

15. The kit of claim 14, wherein the anterior plate includes at least one hole for receiving a bone screw.

16. The kit of claim 14, wherein the angle adjustment instrument includes pins dimensioned to engage pin holes in the expandable disc replacement body, the pins allowing the angle adjustment instrument to apply torque to the expandable disc replacement body to open the expandable disc replacement body to the angle.

* * * * *